US007341565B2

(12) United States Patent
Splane, Jr. et al.

(10) Patent No.: US 7,341,565 B2
(45) Date of Patent: Mar. 11, 2008

(54) PASSIVE MOTION MACHINE PROVIDING CONTROLLED BODY MOTIONS FOR EXERCISE AND THERAPEUTIC PURPOSES

(75) Inventors: Robson L. Splane, Jr., Valley Center, CA (US); John R. Santarsiero, Jr., Stewart, FL (US)

(73) Assignee: Suncepts, Inc., Stuart, FL (US)

( * ) Notice: Subject to any disclaimer, the term of this patent is extended or adjusted under 35 U.S.C. 154(b) by 524 days.

(21) Appl. No.: 10/815,970

(22) Filed: Apr. 2, 2004

(65) Prior Publication Data

US 2005/0222523 A1 Oct. 6, 2005

(51) Int. Cl.

*A61H 1/00* (2006.01)
*A61H 1/02* (2006.01)
*A61H 5/00* (2006.01)
*A61F 5/00* (2006.01)

(52) U.S. Cl. .............................. 601/5; 601/24; 601/25; 601/26; 601/34; 601/35; 601/39; 602/245

(58) Field of Classification Search .................... 601/5, 601/23, 24–26, 34, 35, 39; 606/237, 240–245; 128/845; 5/600, 933, 618

See application file for complete search history.

(56) References Cited

U.S. PATENT DOCUMENTS 3,450,132 A * 6/1969 Ragon et al. ................. 601/26
3,620,210 A * 11/1971 Annas et al. ............... 606/245
3,674,017 A 7/1972 Stefani, Jr.
4,144,880 A 3/1979 Daniels
4,827,913 A 5/1989 Parker
4,953,541 A * 9/1990 Parker, Jr. .................... 601/35
5,035,234 A 7/1991 Forsythe
5,044,359 A 9/1991 Reinert
5,099,828 A * 3/1992 Duke .......................... 601/26
5,123,916 A 6/1992 Riddle et al.
5,171,260 A 12/1992 McIlwain
5,300,090 A * 4/1994 Primic ......................... 601/26
5,308,359 A * 5/1994 Lossing ...................... 606/242
5,320,640 A * 6/1994 Riddle et al. ............... 606/242
5,320,641 A 6/1994 Riddle et al.
5,500,002 A 3/1996 Riddle et al.
5,926,002 A * 7/1999 Cavanaugh et al. ........ 318/672
6,086,550 A 7/2000 Richardson
6,446,287 B2 * 9/2002 Borders ......................... 5/618
6,692,451 B2 2/2004 Splane, Jr.

* cited by examiner

*Primary Examiner*—Justine R. Yu
*Assistant Examiner*—Kristen C. Matter
(74) *Attorney, Agent, or Firm*—Stites & Harbison PLLC; Ross F. Hunt, Jr.

(57) ABSTRACT

A passive motion exercise and/or treatment apparatus is provided which includes a main support assembly for supporting at least the head and torso of a user. The main assembly includes three support members which, in one mode of operation, are disposed in a common plane. The second and third members are movably connected to the first member, which is a backrest support member, and are movable relative thereto so as to respectively provide passive movement of both the head and, and the lumbar region, of a user. Cervical side bending and rotational movements and lumbar side bending and rotational movements can all be provided. A separable leg support assembly is adjustable to support the calves of the user in a plane elevated with respect to the common plane while the apparatus provides the aforementioned passive body movements.

41 Claims, 21 Drawing Sheets

FIG. 38
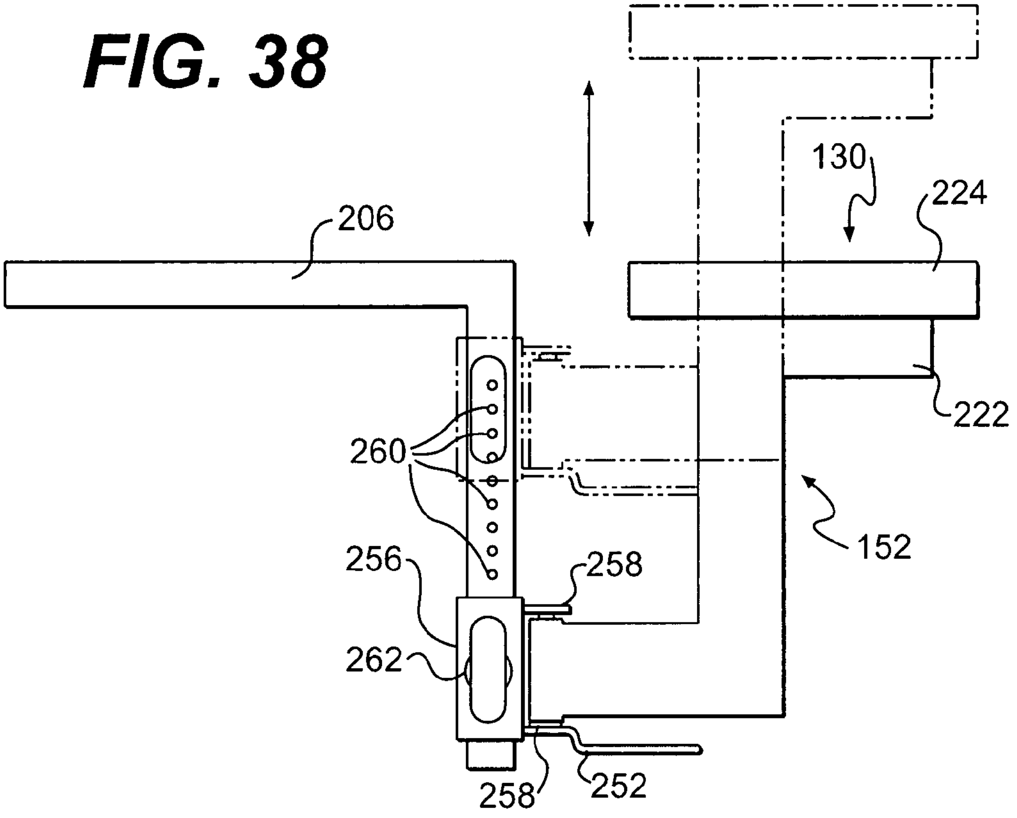
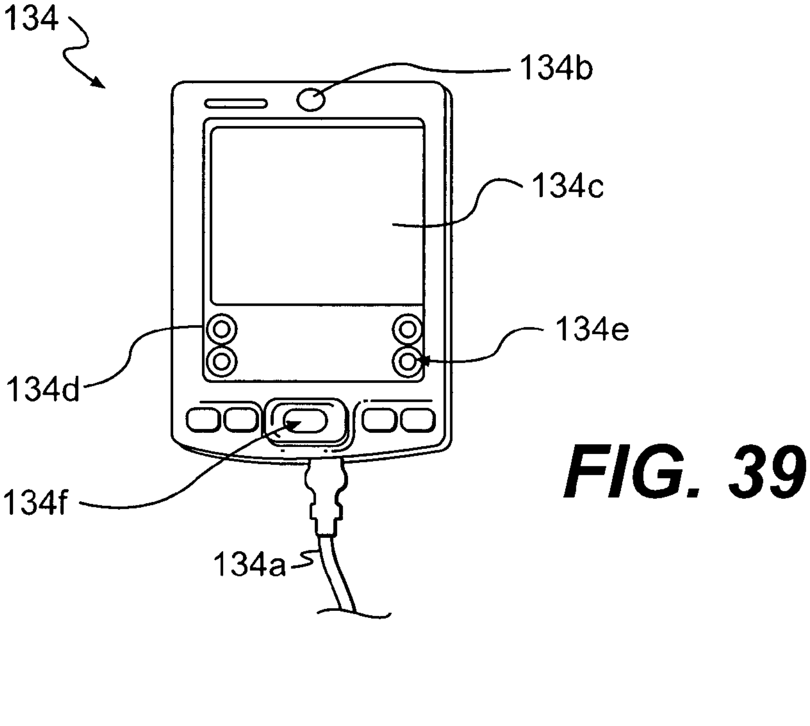
FIG. 39

PASSIVE MOTION MACHINE PROVIDING CONTROLLED BODY MOTIONS FOR EXERCISE AND THERAPEUTIC PURPOSES

FIELD OF THE INVENTION

The present invention relates to exercise and therapeutic devices and, more particularly, to passive motion devices, i.e., devices which put a passive user through prescribed movements without effort on the part of the user.

BACKGROUND OF THE INVENTION

It is estimated that in the United States alone, as of the mid-1990s, there were 25,000,000 people a day who suffered from some kind of back pain and that as many as nine out of ten Americans will suffer back pain at some time in their lives. The resultant total economic burden on industry in the United States is estimated at $40 to $50 billion annually.

One approach to relieving back pain and cervical pain is through exercise or therapeutic movement, and a substantial number of exercise devices and machines have been developed for exercising the back. However, many of these devices are unsuitable for persons suffering from serious back pain because use thereof tends to increase the pain and/or because there is danger of injury (or further injury) to the back, e.g., to the spine or to the supporting muscles.

One approach to exercising of the back and other parts of the body involves the use of passive exercise machines, i.e., machines that exercise muscles of the user (e.g., the back and abdominal muscles) without any active effort on the part of the user. A number of these devices and machines include separate support sections for supporting different parts of the body (e.g., the head and upper torso are supported on one section and the lower torso and legs on a second section) and are motorized so that, e.g., while the user lies flat on his or her back, the lower torso and legs are moved as a unit with respect to the upper torso and head which remain stationary, so as to provide automatic side flexion. Such machines include conventional "toning tables" as well as specially designed devices such as the "electric flexion distraction table" made by Health Care Manufacturing of Springfield, Mo. and the SPINALATOR® machine made by the Chattanooga Group, Inc. of Hixon, Tenn.

Patented devices of interest include those disclosed in U.S. Pat. No. 5,500,002 (Riddle et al.); U.S. Pat. No. 5,320,641 (Riddle et al.); U.S. Pat. No. 5,123,916 (Riddle et al.); U.S. Pat. No. 4,827,913 (Parker); U.S. Pat. No. 4,144,880 (Daniels); U.S. Pat. No. 6,086,550 (Richardson); U.S. Pat. No. 4,953,541 (Parker, Jr.); U.S. Pat. No. 5,044,359 (Reinert); U.S. Pat. No. 5,171,260 (McIlwain); U.S. Pat. No. 5,035,234 (Forsythe); and U.S. Pat. No. 3,674,017 (Stefani, Jr.). Briefly considering some of these patents, the Riddle et al. patents all disclose passive exercise devices designed for the lower back region. The devices feature two sets of support means, one for the upper body and one for the lower body. The device is designed such that either one, or both of the two support means may be pivoted up or down. The Parker patent discloses a passive exercise device which includes interchangeable components adapted to be attached to the table apparatus. The device is deigned to provide leg exercises in a variety of different positions. The Daniels patent discloses a passive traction/motion device. A cervical traction device is also provided. The Richardson patent discloses a passive exercise device in which the patient may be reclined in the so-called "90/90" position described below. The legs of the patient are placed in a leg rest which may be removed from a table portion. The device provides a variable speed rocking motion (in an elliptical path) to the legs and torso of the user.

An important advance in continuous passive motion machines is disclosed in commonly assigned U.S. Pat. No. 6,692,451 (Splane). This patent is discussed in more detail below.

SUMMARY OF THE INVENTION

In accordance with the invention, a continuous passive motion apparatus or machine is provided which affords a number of important improvements or advantages over the prior art. As with U.S. Pat. No. 6,692,451, this invention is based, in part, on the appreciation that continuous passive motion can be beneficial in treating various muscular and skeletal injuries or disorders, and on the belief held by many health care professionals that the slow and passive movement of an injured joint or like disorder can reduce pain and/or speed the recovery of many patients with such disorders.

In accordance with one aspect of the invention, there is provided a continuous passive motion apparatus or machine, the apparatus comprising:

a main support assembly for supporting at least part of the body of a user of the apparatus and including a first support member for, in one mode of use of the apparatus, providing a substantially horizontal support surface defining a plane and a second support member, for, in one mode of use of the apparatus, providing a substantially horizontal support surface disposed in said plane, said second support member being pivotable relative to said first support member such that pivoting movement of the second support member in said plane with respect to the first support member provides passive bending movement of a part of the body of a user supported by said second support member relative to a part of the body supported by said first support member, said second support member having a central axis and further being rotatable about said central axis to provide rotational movement of a part of the body supported by said second support member; and motorized drive means for, when activated, selectively providing said pivoting movement of said second support member relative to said first support member on a continuous, cyclically repeated basis to provide continuous passive bending movement of the part of the body supported by said second support member and selectively providing rotational movement of said second support member on a continuous cyclically repeated basis to provide continuous passive rotational movement of the part of the body supported by said second support member.

Preferably, the apparatus further comprises a calf support assembly connected to said main support assembly at one end of said main support assembly so as to support at least part of the legs of the user, said calf support assembly being connected to said main support assembly by an articulated connection for enabling said calf support assembly to be at least partially stowed away so as to enable a user to be positioned on said main support assembly without interference from said calf support assembly. Advantageously, the calf support assembly includes a support platform and the articulated connection is movable to a position wherein said platform is supported in a plane elevated with respect to the first-mentioned plane such that lower portions of the legs of the user are elevated with respect to the remainder of the body of the user and such that upper portions of the legs of the user extend at substantially right angles with respect to the lower portions of the legs and the trunk of the body of the user. Preferably, the articulated connection of said calf support assembly includes at least two pivotable links for enabling movement of said support platform into the first-mentioned plane and for enabling the spacing between said calf support assembly and said main support assembly to be varied.

Preferably, the motorized drive means comprises at least one electric drive motor and control means for selectively controlling the operation of said at least one motor. Advantageously, the control means comprises programmable means for controlling the at least one motor so as to control the amount of pivoting movement of said second support member relative to said first support member. Preferably, the control means includes a stop switch adapted to be operated by a user of the apparatus undergoing said passive movement to terminate the relative pivoting movement of said second support member.

More generally, the motorized drive means preferably comprises a first motor for providing said pivoting movement and a second motor for providing said rotational movement.

Preferably, the apparatus further comprises a pair of laterally spaced arm rests affixed to said main support assembly for movement relative thereto.

In a preferred implementation, the main support assembly comprises a first part, and a second part selectively pivotable about a horizontal axis with respect to the first part between an inclined position and an upright position. Advantageously, the second support section is adapted to support the lumbar region of the body of a user and forms at least a portion of said first part. Preferably, the apparatus further comprises a pair of laterally spaced arm rests affixed to said main support assembly for movement relative thereto such that said arms lie alongside the main support assembly in said inclined position and are disposed adjacent said second support section so as to form armrests in said upright position.

In one important implementation, the second support member is selectively tiltable to a position wherein said second elevated support member forms a non-zero angle with respect to said first support member.

According to a further aspect of the invention, there is provided a passive motion apparatus for providing passive motion of at least the lower trunk and legs of a user relative to the remainder of the body of the user, the apparatus comprising:

a first elevated support member for, in use, supporting at least an upper trunk portion of a user;

a second elevated support member, movable with respect to said first support member, and disposed, in one use of the apparatus, at a common level with, and adjacent to, said first support member, for, in use, supporting the lumbar region of the user;

a third elevated support member, selectively movable to a plane elevated with respect to said common level and disposed adjacent to said second support member, for supporting lower portions of the legs of the user; and motor means for, when activated, selectively providing continuous cyclically repeated pivotable movement of said second support member about a first pivot axis between spaced end positions so as to provide continuous passive bending motion of the lumbar region of the user and for, when activated, selectively providing continuous cyclically repeated rotational movement of said second support member about a second pivot axis orthogonal to said first pivot axis so as to provide continuous passive rotational motion of the lumbar region of the user.

Preferably, the apparatus further comprises a further elevated support member, movable with respect to said first support member and disposed, in one mode of use of the apparatus, at a common level with, and adjacent to, said first support member, for, in use, supporting at least a portion of the head of the user, said second support member being mounted for pivotable movement relative to said first support member, said motor means, when activated, selectively providing continuous cyclically repeated pivotable movement of said further support member about a vertical axis between spaced end positions so as to provide continuous passive bending motion of the cervical region of the body of the user.

The motor means preferably comprises a separate motor and motor drive assembly for said second support member for, when activated, providing said continuous cyclically repeated rotational movement of the lumbar region of the user supported on said second support member.

In one important implementation, the apparatus further comprises motorized cervical rotation means for said further support member for, when activated, providing continuous cyclically repeated rotational movement of the neck and head of a user between first and second end positions.

The third elevated support member preferably comprises a support platform and includes means for pivotably mounting said support platform with respect to said third support member so as to enable angular and longitudinal adjustment of the support platform relative to the first support member.

Preferably, the second or further support member is selectively tiltable to a position wherein said second support member forms a non-zero angle with respect to said first support member.

The apparatus preferably further comprises control means for said motor means for, when activated, simultaneously providing both said pivotable movement and said rotational movement.

In accordance with yet another aspect of the invention, there is provided a continuous passive motion apparatus, the apparatus comprising:

a main support assembly for supporting at least part of the body of a user of the apparatus and including a first support member for providing a substantially horizontal support surface defining a first plane, a second support member for, in one configuration of the apparatus, providing a second support surface disposed in said plane, a third support member including for, in said one configuration of said apparatus, providing a third support surface disposed in said plane, said second and third support members each being pivotably mounted so as to be movable, in said one configuration, in said plane relative to said first support member such that pivoting movement of the second and third support members with respect to the first support member provides passive bending movement of a respective part of the body of a user supported by said second and third members relative to a part of the body supported by said first support member, said second and third support members each being further pivotably mounted about a respective central pivot axis thereof so as to enable rotation of the support surface thereof about said central pivot axis such that rotational movement of said second and third members provides passive rotational movement of a respective part of the body of a user supported by said first support member;

a leg support assembly connected to said main support assembly at one end of said main support assembly so as to support at least part of the legs of the user, said leg support assembly being movable to a second plane elevated with respect to said first plane;

motorized drive means for, when activated, selectively providing continuous cyclically repeated pivoting movement of said second and third support members about the respective vertical axes thereof relative to said first support member and selectively providing continuous cyclically repeated rotational movement of said second and third support members about the respective central pivot axes thereof relative to said first support member.

Preferably, the motorized means comprises a first motor for providing pivoting movement of said second support member, a second motor for providing pivoting movement of said third support member, a third motor for providing rotational movement of said second support member, a fourth motor for providing rotational movement of said third support member and programmable means for controlling selective activation of said first, second, third and fourth motors.

The second support member is, preferably, selectively tiltable to a position wherein said second elevated support member forms a non-zero angle with respect to said first support member.

Similarly, the third support member is, preferably, tiltable to a position wherein said third support member forms a non-zero angle with respect to said first support member.

According to a further aspect of the invention, there is provided a continuous passive motion apparatus, the apparatus comprising:

a body support unit comprising:

at least one support member for, in use, supporting at least the upper trunk and head of a user;

a second support member, movable with respect to said at least one support member and disposed adjacent to said at least one support member, for, in use, supporting the lumbar region of the user;

a third support member, disposed adjacent to said second support member and movable to a different plane therefrom, for engaging the calf portions of the legs of the user; and motor means for, when activated, at least providing continuous cyclically repeated lateral pivoting movement of said second and third support members together, relative to said at least one support member;

a stationary base for supporting said body support unit; and means for selectively providing pivoting of said at least one support member of said body support unit relative to said stationary base, and said second and third support members, between a first position wherein, in use, a user is supported in seated posture on the second support member of the said body support unit with the upper trunk and head resting against said at least one support member, and a second, substantially horizontal position wherein, in use, a user is supported in a reclining posture on said body support unit.

Preferably, the at least one support member comprises a first support member for supporting the head of a user and a further support member for supporting the upper trunk of a user.

The at least one support member and said second support member are, preferably, pivotably relative to each other so as to form a non-zero angle therebetween in the first position of said body support unit.

Advantageously, the second support member extends outwardly at a non-zero angle with respect to said at least one support member so as to act as a seat in said first position of said body support unit.

Preferably, the at least one support member of said body support unit includes a first support member for supporting the head of a user and a further support member for supporting at least the upper trunk of a user, and the apparatus further comprises movement control means for providing continuous cyclically repeated lateral pivotable movement of the first support member with respect to said further support member. Advantageously, the movement control means further comprises cervical rotation means for controlling movement of said first support member so as to provide rotational movement of the head and neck of the user. Preferably, the movement control means controls movement of said first member so as to produce continuous, cyclically repeated rotational movement of the head and neck of the user between first and second end positions.

Preferably, the apparatus further comprises cervical rotation means for said first support member for, when activated, providing continuous, cyclically repeated rotational movement of the neck and head of a user between first and second end positions.

Advantageously, the passive motion further comprises control means for controlling movement of said second and third support members to produce continuous, cyclically repeated rotational movement between first and second end positions of the part of the body received on said second and third support members. Advantageously, the control means comprises a handheld computer for enabling of control speed, direction and amount of pivoting movement and speed, direction and amount of rotational movement.

In an important implementation, the handheld computer further enables setting of a time period for said pivoting movement and for said rotational movement.

In accordance with yet another aspect of the invention, there is provided a continuous passive motion apparatus, said apparatus comprising:

a main support assembly for supporting at least part of the body of a user of the apparatus and including first, second and third support members for supporting different parts of the body of the user, at least one of said support members being pivotably mounted and being movable relative to the remaining support members of the main support assembly such that movement of the at least one support member with respect to the remaining support members provides passive movement of a part of the body of a user supported by said at least one member relative to a part of the body supported by the remaining support members;

motorized drive means for, when activated, providing said movement of said at least one support member relative to said remaining support members on a continuous, cyclically repeated basis to provide continuous passive movement of the part of the body supported by said at least one support member;

said at least one of said support members of said main support assembly being adapted to support the head of a user thereon and said apparatus further comprising motorized cervical rotation means for said at least one support member of said main support assembly for, when activated, providing continuous, cyclically repeated, rotational movement of the at least one support member about a rotational pivot axis s as to provide passive rotational movement of the neck and head of the user when the head of a user is supported on said at least one support member.

Preferably, the passive motion apparatus further comprises a leg support assembly connected to said main support assembly at one end of said main support assembly and adjustable to support lower portions of the legs of the user in an elevated plane relative to said main support assembly such that the lower portions of the legs of the user are elevated with respect to the remainder of the body of the user;

Further features and advantages of the present invention will be set forth in, or apparent from, the detailed description of preferred embodiments thereof which follows.

BRIEF DESCRIPTION OF THE DRAWINGS

FIG. 38 is a simplified side elevational view of a portion of the cervical section of FIG. 25, showing a vertical adjustment feature;

FIG. 39 is a front elevational view of a preferred embodiment of the handheld controller of FIG. 25;

DESCRIPTION OF THE PREFERRED EMBODIMENTS

Figure 1:
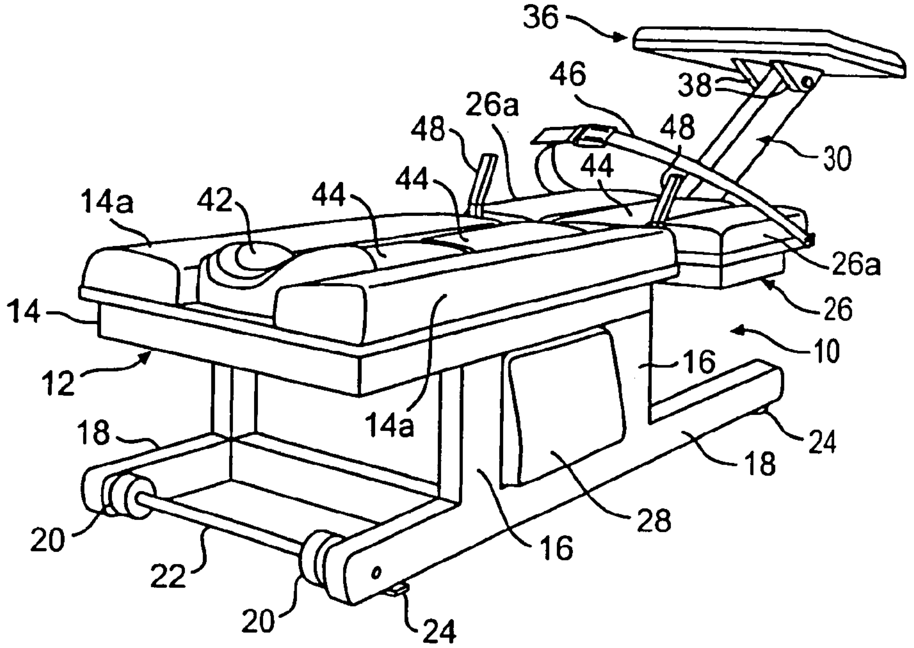
FIG. 1 PRIOR ART
FIG. 1 is a perspective view of a passive range of motion exercise and/or treatment apparatus in accordance with a preferred embodiment of U.S. Pat. No. 6,692,451.

Referring to FIGS. 1 to 6, there is shown a preferred embodiment of the continuous passive motion and traction device as disclosed in U.S. Pat. No. 6,692,451. As indicated in FIG. 1, the device or machine, which is generally denoted 10, includes a frame 12 including an upper main table member 14 supported by legs 16 or like supports in a sled configuration formed by parallel support members 18. Wheels 20 mounted on a transverse axle 22 extending between the front ends of support members 18 enable the device 10 to be moved. Downwardly depending, adjustable leveling elements or levelers 24 located at the ends of support members 18 help fix the device 10 in place as well as to level the device. Levelers 24 are provided at both ends of support members 18 in FIG. 1 and at only one end in FIG. 2 and either option can be used.

Figure 2:
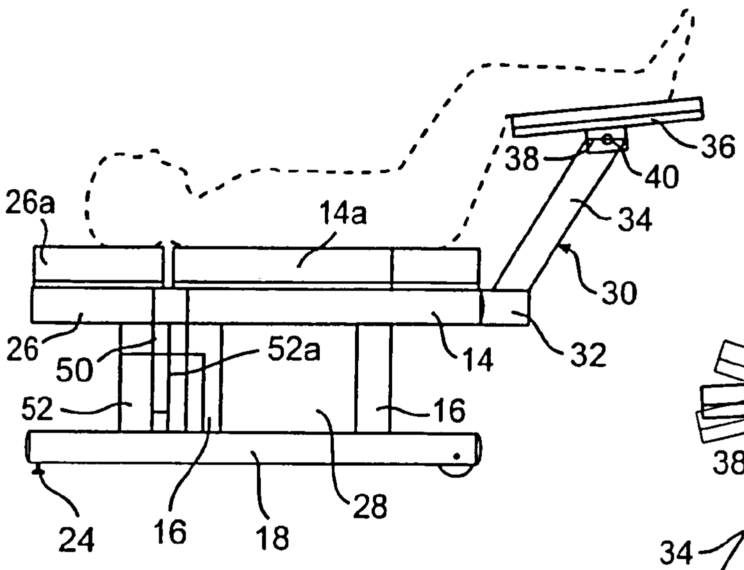
FIG. 2 PRIOR ART
FIG. 2 is a side elevational view of the device of FIG. 1 showing a different component configuration.

In the configuration shown in FIG. 1, the overall support portion of device 10 includes the aforementioned main table member 14 and a further auxiliary, upper support member 26 which is located adjacent to the foot or distal end of main table member 14. Support member 26 is of a smaller size than, and is movable (pivotable) with respect to, table support member 14. In the configuration shown in FIG. 1, support member 26 is positioned at what would be considered the foot or distal end of table member 14, and, in this configuration, at the foot of device 10, as shown in FIG. 1. In another configuration, which is used to provide movement of the neck and head of the user, support member 26 is positioned at what would be considered to be the head or proximal end of the device 10, as shown in FIG. 2. As described hereinbelow, the particular relative orientation of support member 26 used is dictated by the mode of operation of device 10.

A control panel or control unit 28 is located beneath main table member 14, on one side thereof, between legs 16 as indicated in FIGS. 1 and 2. Control unit 28 contains an electrical control system for the operating mechanisms described below, including the controls of the simplified control circuit shown in FIGS. 7 and 8. It will be appreciated that the control panel or control unit can be a separate unit from the main apparatus and that the control unit can also be connected to an external computer device such as a PC.

Figure 3:
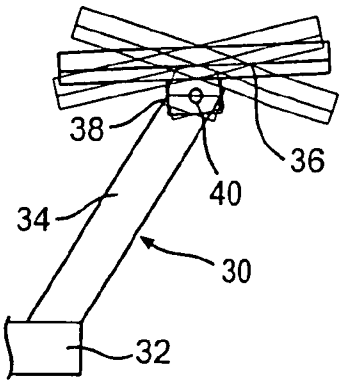
FIG. 3 PRIOR ART
FIG. 3 is a side elevational view of the lower leg (calf) support assembly of FIGS. 1 and 2.
Figure 6:
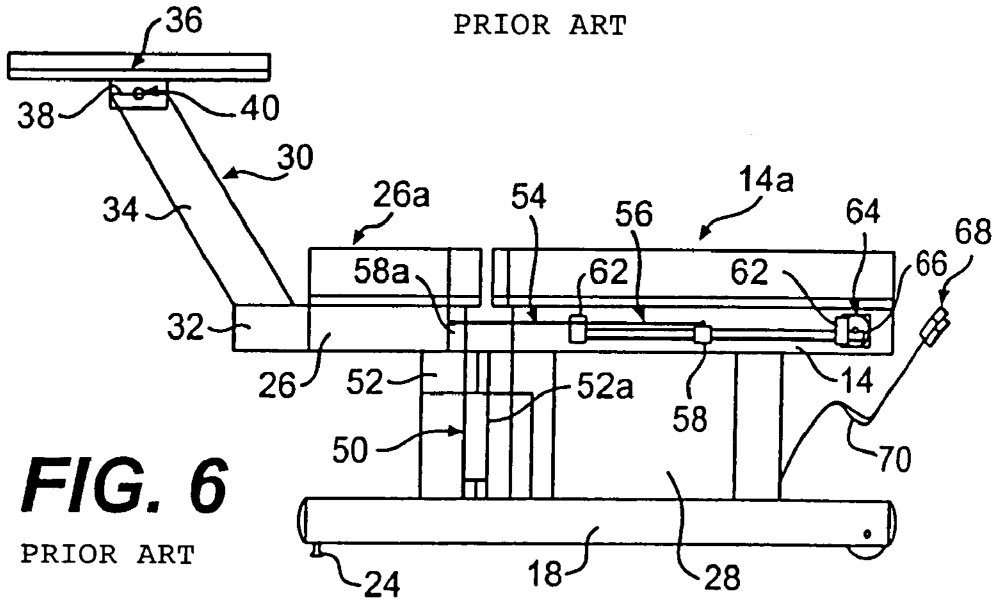
FIG. 6 PRIOR ART
FIG. 6 is a side elevational view of the apparatus of FIG. 5.

An adjustable, self-adjusting lower leg (calf) support assembly 30 is also provided which can be moved to either end of device 10 in different modes of operation described below. Calf support assembly 30 can also be completely removed from the device 10 for shipping or storage. Calf support assembly 30 includes a base member 32 which includes conventional mounting means (not shown) for mounting base member 32, and thus the entire assembly 30, on either main table member 14 as shown in FIG. 2 or on auxiliary support member 26 as shown in FIGS. 1 and 6. The mounting means (not shown) can take a number of different forms and can, for example, comprise a shaped (e.g., square) mounting element (not shown) adapted to be non-rotatably and detachably received in a corresponding slot or sleeve (not shown) provided at the free end of each of the support members 14 and 26. Support assembly 30 further includes a connecting member or strut 34 and a support platform 36 which is of a double plate construction in the illustrated embodiment. A pair of mounting elements 38 (see FIG. 1) are secured to strut member 34 by a pivot pin 40 so as to enable pivoting of platform 36 about pivot pin 38, as indicated in FIG. 3. The mounting arrangement for platform 36 is such that the platform 36 can be pivoted by corresponding movement of the calves and feet of the user, and thus is readily self-adjusting, yet is still stiff enough that the platform 36 will remain in the position to which it is moved. Again, the pivotable mounting arrangement is conventional per se and it will be understood by those skilled in the mechanical arts that a number of different pivotable mounting arrangements are suitable for this purpose.

Figure 4:
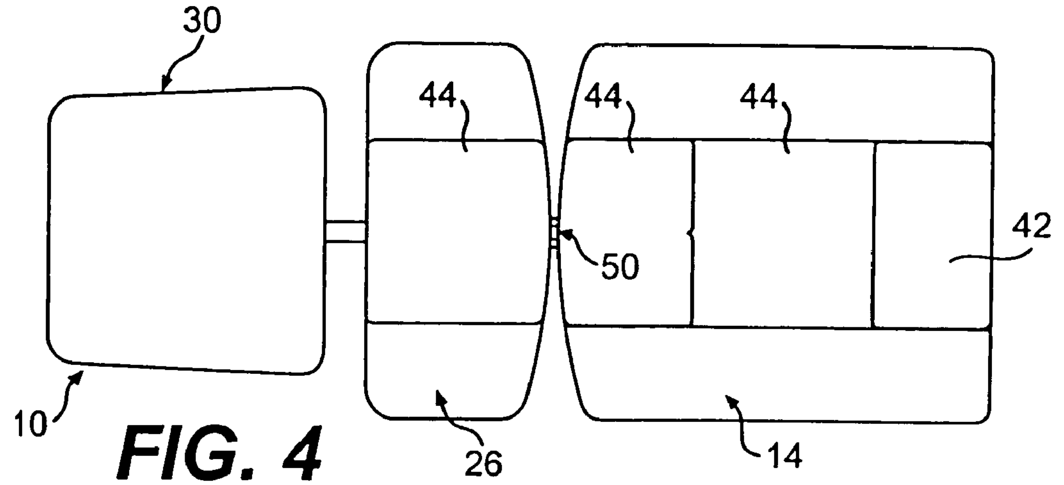
FIG. 4 PRIOR ART
FIG. 4 is a top plan view of the apparatus of FIG. 1, showing certain optional features thereof.

As best seen in FIGS. 1 and 4, the table support member 14 and auxiliary support member 26 include spaced pairs of contoured pads 14*a* and 26*a*, respectively, mounted thereon. Further, in the exemplary embodiment illustrated, a head pillow 42 is disposed between pads 14*a* at one end thereof and a series of removable, replaceable hot and/or cold packs 44 are disposed between pads 14*a* and 26*a*, as illustrated in FIG. 4. Pads 14*a* and 26*a* are preferably fabricated of a contoured foam although other materials may be used. The hot and/or cold packs 44 are used to apply heat or cold to different parts of the body of the user (e.g., the back and buttocks or the sides and hips) as appropriate to his or her condition and treatment schedule (e.g., whether the application of heat and/or cold is prescribed in connection with a particular exercise or treatment regimen).

As indicated in FIG. 1, a seat belt 46, or like restraining belt or harness, is preferably provided on auxiliary support member 26 so as to hold the waist and hips in place during certain movements. In addition, in an optional embodiment also shown in FIG. 1, a pair of handle grips or hand grips 48 are provided which extend upwardly and outwardly from table member 14 at the end thereof adjacent to support member 26 so as to be grippable by a user during certain movements. The hand grips can also be provided on the support member 26 and this may be preferable in some applications.

As indicated above, auxiliary support member 26 is pivotable with respect to table member 14 and, to this end, an upright pivot shaft 50 is provided about which support member 26 pivots. As will be understood by those skilled in the mechanical arts, the overall pivoting arrangement can take a number of different conventional forms. For example, a simple arrangement can be used wherein a downwardly depending portion 52 of support member 26 includes a sleeve 52*a* which is affixed to the depending portion 52 that faces pivot shaft 50 and which fits around pivot shaft 50 to enable pivoting of auxiliary support member 26 relative to table support member 14.

Figure 5:
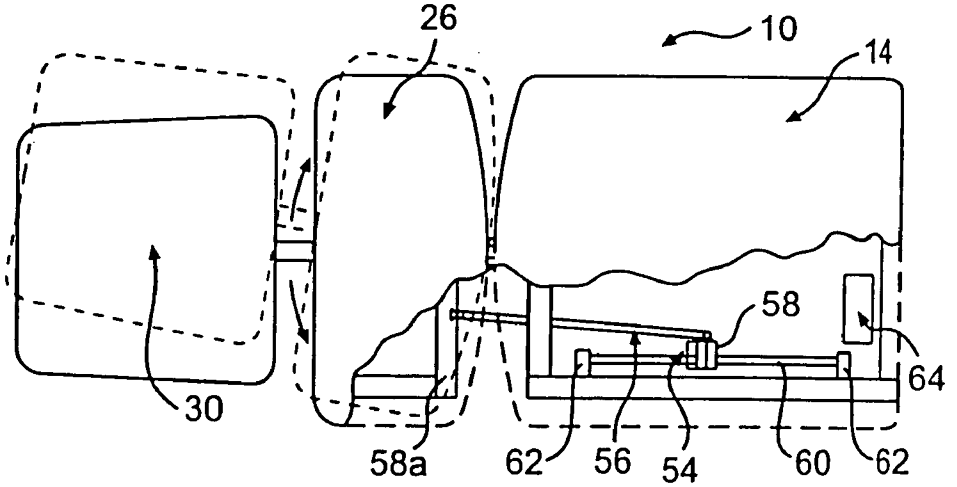
FIG. 5 PRIOR ART
FIG. 5 is a further top plan view of the apparatus of FIG. 1, partially broken away to show the operating mechanism therefor and with the optional features of FIG. 4 omitted.

A preferred embodiment of the operating mechanism for pivoting support member 26 is generally indicated at 54 in FIGS. 5 and 6. The operating mechanism 56 includes a linkage member 56 which is pivotably connected at one end thereof to a frame portion 26*a* of support member 26 and at the end thereof to a traveling nut 58 mounted on a rotatable worm gear or screw 60 rotatably mounted in first and second spaced bushings 62. Gear or screw 60 is driven by a gear head motor 64 with an eccentric drive element 66. Rotation of screw 60 produces movement of traveling nut 58 therealong, with the direction of rotation of screw 60 determining the direction of travel of nut 58. This movement of nut 58 produces corresponding movement of linkage member 56 and thereby causes pivoting of support member 26.

It will, of course, be understood that, as discussed in U.S. Pat. No. 6,692,451, other operating mechanisms can be used and, in this regard, in another, non-illustrated embodiment, the eccentric drive element 66 is used to drive a spring biased crank arrangement (not shown). The user can exert a resistive force against the springs (not shown) of this arrangement to provide interactive exercising of the body part in question, and an override feature can be provided, if desired, wherein the user can overpower the machine. It will, of course, be understood that the motor or drive unit that is used in these various embodiments can be other than an electric motor (e.g., a hydraulic motor or the like).

As indicated above, the electronic controls for motor 64 are housed within control panel or unit 28. As shown in FIG. 6, a remote control, hand operated switch device 68 is connected to control unit 28 by a cable 70 so as to enable the operation of the device 10 to be controlled by the user during use. In a preferred embodiment, switch device 68 is, or includes, a “kill” switch, i.e., a switch that enables the user to immediately stop operation of the device 10, and thus immediately terminate an exercise when, e.g., the user is feeling overtired or is suffering pain. Optionally, other functions, such as motor speed, can also be controlled by switch device 68.

Figure 7:
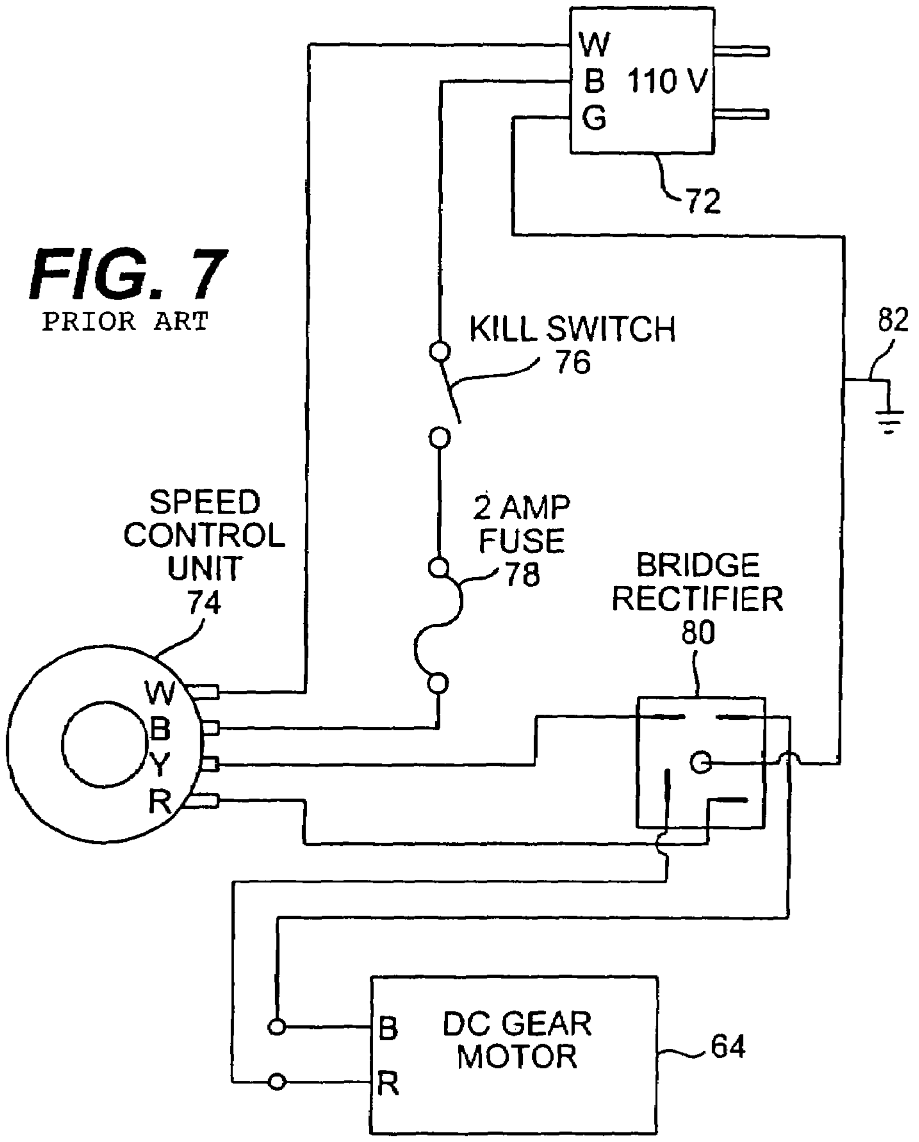
FIG. 7 PRIOR ART
FIG. 7 is a schematic circuit diagram of a preferred embodiment of a control circuit for the apparatus of FIG. 1.

Referring to FIG. 7, a schematic circuit diagram of the motor control circuit is shown. The circuit includes a (110 volt) wall plug 72 two leads of which are connected to a speed control unit 74, with one lead (the B lead) being connected through a "kill" switch 76 and a fuse 78. Two output leads from speed control unit 74 are connected through a bridge rectifier unit 80 to the DC gear motor 64 mentioned above. A ground connection indicated at 82 is preferably made to the frame of device 10 through the mount (not shown) for the full wave bridge unit 80.

Figure 8:
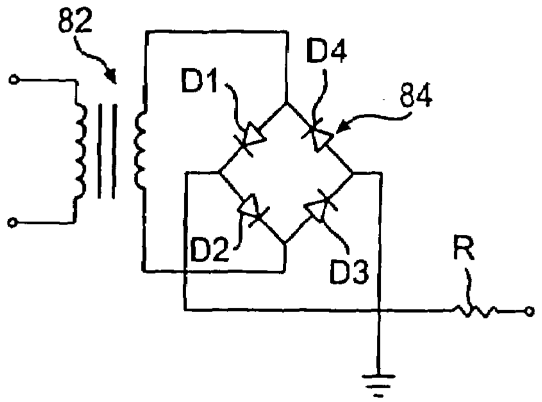
FIG. 8 PRIOR ART
FIG. 8 is a schematic circuit diagram of a preferred embodiment of one unit (the bridge rectifier unit) of the circuit of FIG. 7.

A schematic circuit diagram of bridge rectifier unit 80 is shown in FIG. 8. As illustrated, unit 80 includes a transformer 82 connected to a full wave diode rectifier bridge 84 comprising diodes D1, D2, D3 and D4. The DC leads from bridge 84 is connected to motor 64, with the non-grounded lead being connected to motor 64 through a resistor R.

It will be understood that the control circuitry of FIGS. 7 and 8 represents a simplified control approach and, in preferred embodiments, more sophisticated adjustments would be provided for controlling speed, power, duration, volume and like parameters, depending on the nature of the operating mechanism used and the operating features desired.

Figure 9:
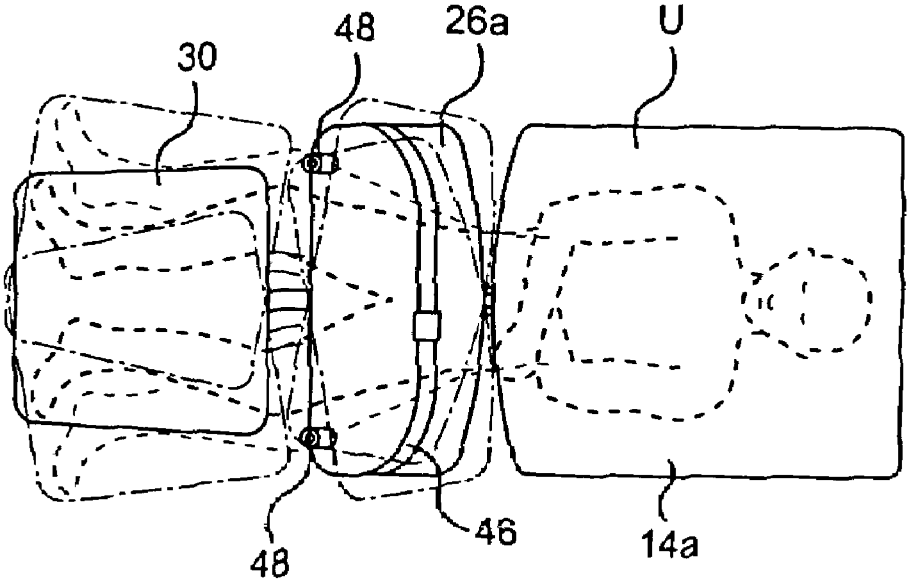
FIG. 9 PRIOR ART
FIGS. 9 and 10 are a top plan view and a side elevational view, respectively, of the apparatus of FIG. 1, showing one mode of operation thereof.
Figure 10:
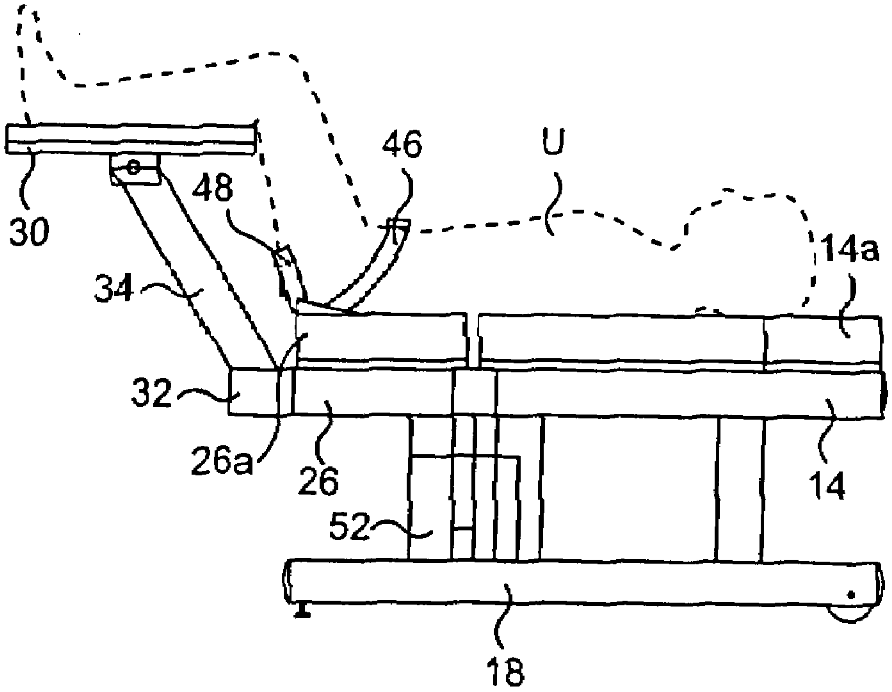
FIG. 10 PRIOR ART

Referring to FIGS. 9 and 10, there is illustrated a first mode of operation of device 10. In this mode of operation, the user U is positioned in the "90/90" position referred to above, wherein the user U lies horizontally on his or her back on table member 14 and the lower legs are supported on platform 36 in a parallel horizontal plane. The buttocks are supported on auxiliary support member 26 in the same horizontal plane as the rest of the body trunk or torso, and both the trunk and lower legs are positioned at an angle of roughly 90° to the substantially vertical upper legs. This "90/90" position is widely regarded as the most comfortable for those with lower back pain.

In the illustrated configuration, the buttocks are, as indicated above, supported on auxiliary support member 26, with the user U being positioned between hand grips 48. Seat belt 46 is placed around the lower trunk to secure the user U in place. In this position, pivoting of support member 26, as indicated in dashed lines in FIG. 9, provides movement of the lower trunk through a limited range of motion and thus provides gentle exercising of the lower back. Stated differently, pivoting of support member 26 can provide from 0-20° (inclusive) of mechanically assisted lateral side flexion for the lumbar spine. It will be understood that the pivoting motion provided can be through the same angle on both sides, different angles on the two sides or on one side only. The general motion provided is widely accepted as being the most tolerable and potentially the most beneficial to individuals suffering from relatively severe back pain, while not producing user discomfort.

Figure 11:
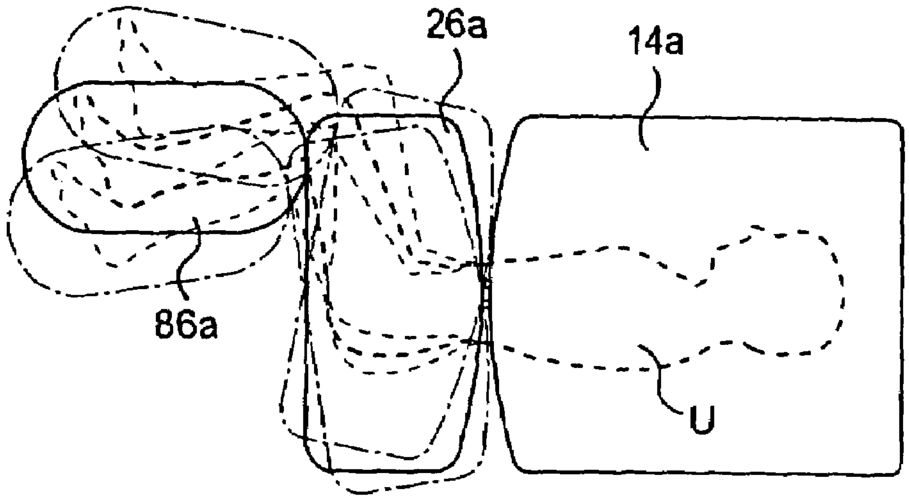
FIG. 11 PRIOR ART
FIGS. 11 and 12 are a top plan view and a side elevational view, respectively, of a modified form of the apparatus of FIG. 1, showing a further mode of operation.
Figure 12:
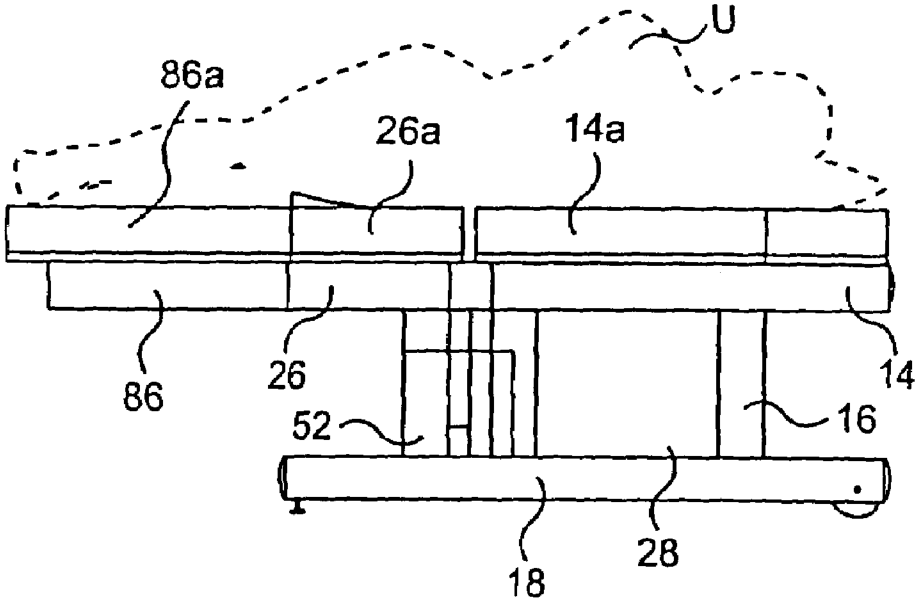
FIG. 12 PRIOR ART

Referring to FIGS. 11 and 12 a further mode of operation is shown. In this embodiment, the lower leg (calf) support assembly 30 is not used, and a different leg support member 86 is provided. Leg support member 86 is adapted to be affixed to support member 26 at one side or the other and as in the other embodiment, a contoured pad or cushion 86*a* is disposed on support member 86. The connection between support member 86 and support member 26 can take a number of different forms. In one embodiment, this connection can comprise a simple rod and sleeve (or slot) connection wherein a downwardly depending portion of a rod (not shown) mounted on one of the two members 86 and 26 is received in a sleeve or slot (not shown) mounted on the other of the members 86 and 26. As indicated above, leg support member 86 is adapted to be mounted at either side of support member 26 so that the user U can be positioned on either side of his or her body. In the mode of operation illustrated, the user U lies on one side, and the hips and lower trunk together with the legs are pivoted relative to the rest of the body.

Figure 13:
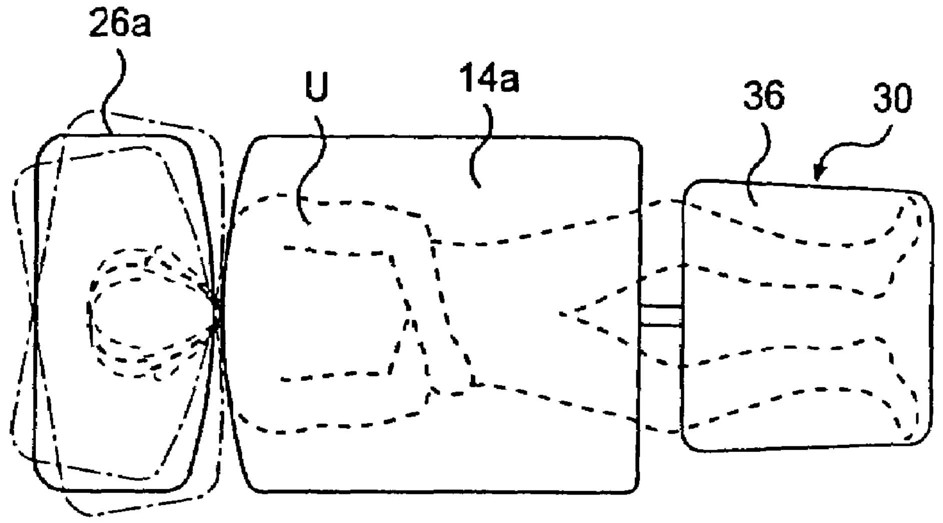
FIG. 13 PRIOR ART
FIGS. 13 and 14 are a top plan view and a side elevational view, respectively, of a different configuration of the apparatus of FIG. 1, showing a further mode of operation.
Figure 14:
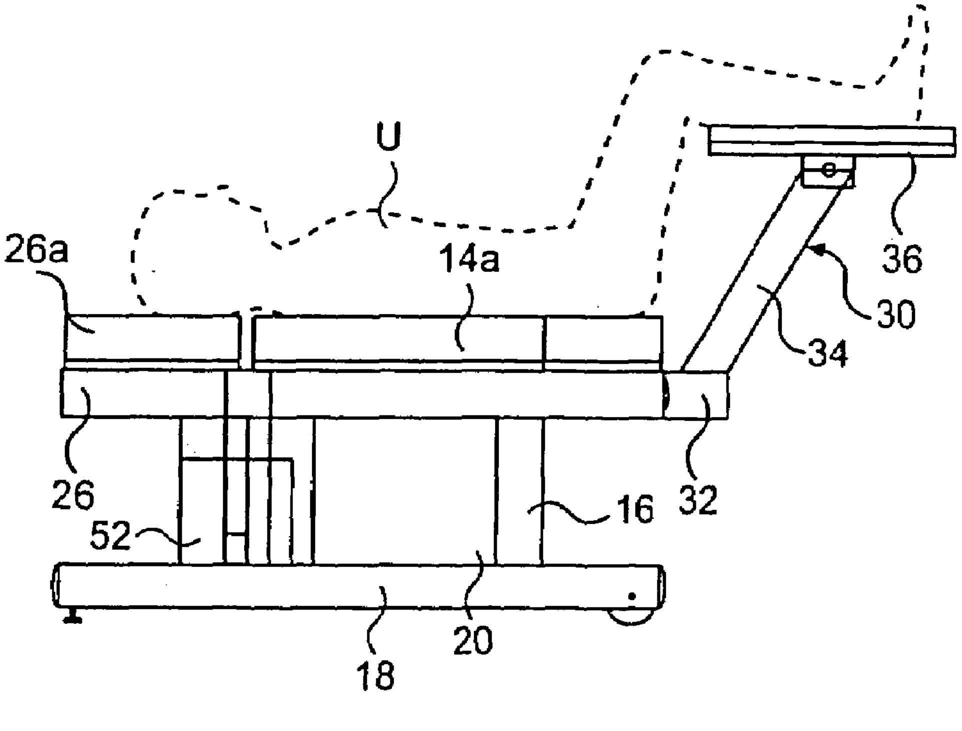
FIG. 14 PRIOR ART

Referring to FIGS. 13 and 14, a further mode of operation is illustrated. In this mode of operation, which employs the configuration illustrated in FIG. 2, the leg (calf) support assembly 30 is not affixed to support member 26 but is rather affixed to the opposite end of table support member 14. The user U is thus supported in the "90/90" position as in FIGS. 9 and 10 but, in contrast to the mode of operation illustrated in FIGS. 9 and 10, the neck and head move relative to the remainder of the body through pivoting movement of support member 26, on which the head of the user U rests.

Figure 15:
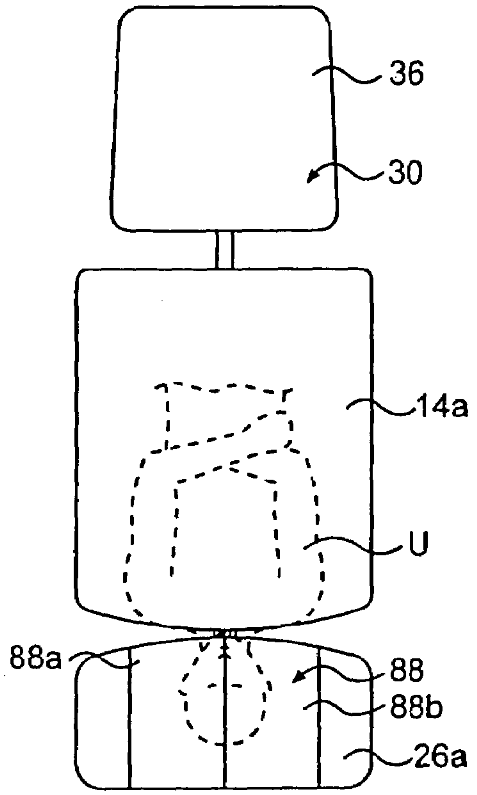
FIG. 15 PRIOR ART
FIGS. 15 and 16 are a top plan view and an end elevational view, respectively, of a modified form of the apparatus of FIG. 1, illustrating yet another mode of operation.
Figure 16:
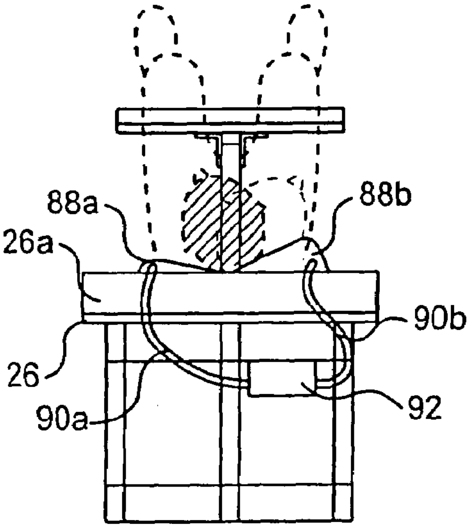
FIG. 16 PRIOR ART

Turning to FIGS. 15 and 16, an embodiment is shown which is also disclosed in U.S. Pat. No. 6,692,451. This embodiment of that patent is somewhat similar to that of FIGS. 13 and 14, and, in this embodiment, support member 26 is provided with an air bladder device 88 used to provide head movement. Bladder device 88 includes two air bladders 88*a* and 88*b* which are disposed in side by side relation, as shown in FIG. 16, and are connected by hoses 90*a* and 90*b* to an air pump 92 with volume, timer and exhaust controls. The pump 92 is used to alternately inflate and deflate bladders 88*a* and 88*b* so that the head is passively moved from side to side as indicated in FIG. 14 and the neck thus exercised by this movement. This can be done in lieu of, or in conjunction with, pivoting movement of the support member 26, depending on the exercise regimen appropriate for the particular user.

Figure 17:
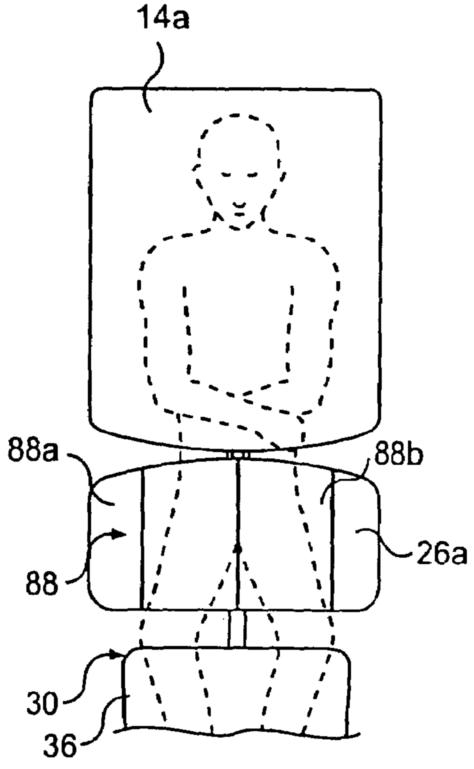
FIG. 17 PRIOR ART
FIGS. 17 and 18 are a top plan view and an end elevational view, respectively, of a further configuration of the apparatus of FIGS. 15 and 16, showing a still further mode of operation.
Figure 18:
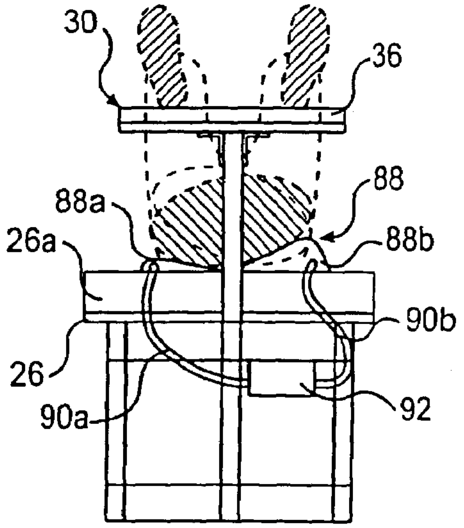
FIG. 18 PRIOR ART

Referring to FIGS. 17 and 18, an embodiment is shown which is also disclosed in U.S. Pat. No. 6,692,451. This embodiment of that patent is similar to that of FIGS. 14 and 15 but in which, instead of the bladder arrangement 88 being used to support the head and neck, the bladder arrangement 88 is used to support the lower trunk. As shown, the leg (calf) support assembly 30 is located at the other end of the device 10 so that the lower trunk rests on pad 26*a* provided on support member 26. This arrangement permits the hips to be rotated as indicated in dashed lines in FIG. 17 by alternatively inflating and deflating bladders 88*a* and 88*b*.

As discussed in U.S. Pat. No. 6,692,451, in a non-illustrated embodiment, a further bladder or expandable section (not shown) is provided which is disposed so as to be positioned under, e.g., the upper back of a user between the shoulder blades. The further bladder (not shown) would be inflated and deflated alternately with a neck supporting bladder to provide a gentle rocking motion.

In order to prevent overinflation of a bladder in a situation where a bladder is partially inflated when the machine is turned off (and thus subject to being overinflated when the machine is turned on again and thus the pressure necessary to provide normal full inflation is applied), in accordance with a further, non-illustrated embodiment, the bladders are automatically deflated when the machine is turned off by means, e.g., of a solenoid-controlled actuator providing such deflation.

Figure 19:
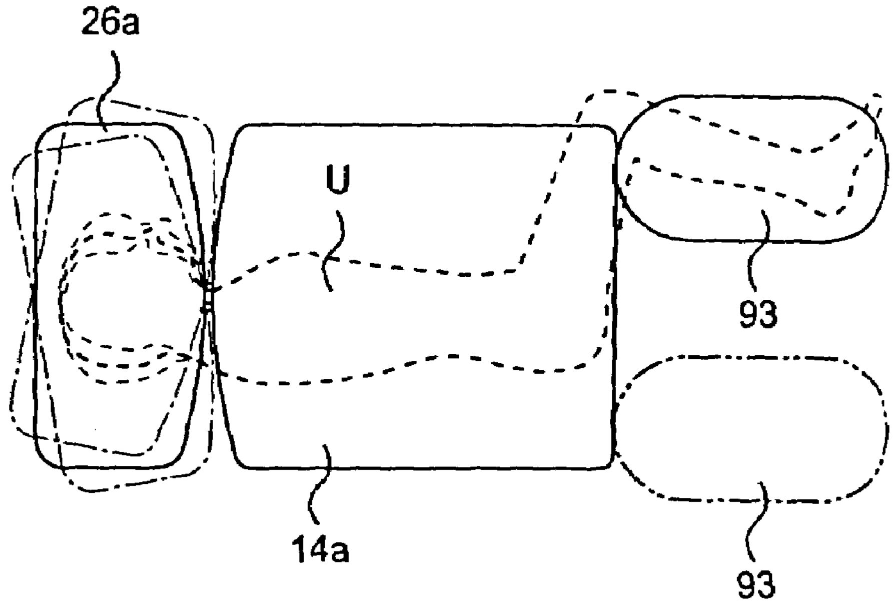
FIG. 19 PRIOR ART
FIGS. 19 and 20 are a top plan view and side elevational view, respectively, of a different configuration of the apparatus of FIGS. 11 and 12, showing another mode of operation.
Figure 20:
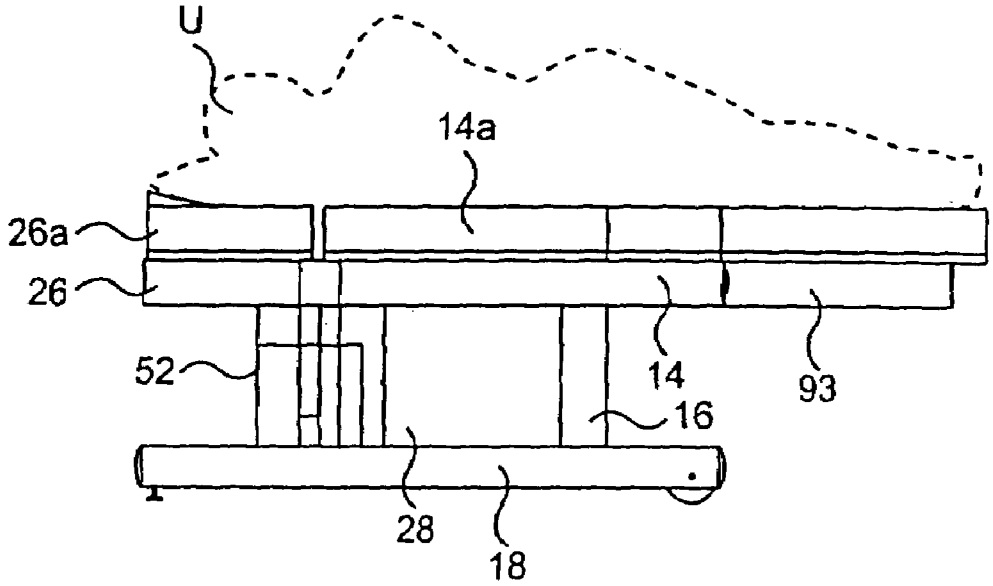
FIG. 20 PRIOR ART

Referring to FIGS. 19 and 20, an embodiment similar to that of FIGS. 11 and 12 of U.S. Pat. No. 6,692,451 is shown. In this embodiment, a leg support member 93, corresponding to leg support member 86 of FIGS. 11 and 12, is affixed to table member 14, rather than auxiliary support member 26 as in FIGS. 11 and 12, and is used to support the legs of user U while the head and neck are moved by pivoting of support member 26 while the user U lies on one side. As indicated in FIG. 18 and was discussed above in connection with FIGS. 11 and 12, leg support member 93 can be positioned at either side of table member 14 so as to permit the user to lie on either side.

Figure 21:
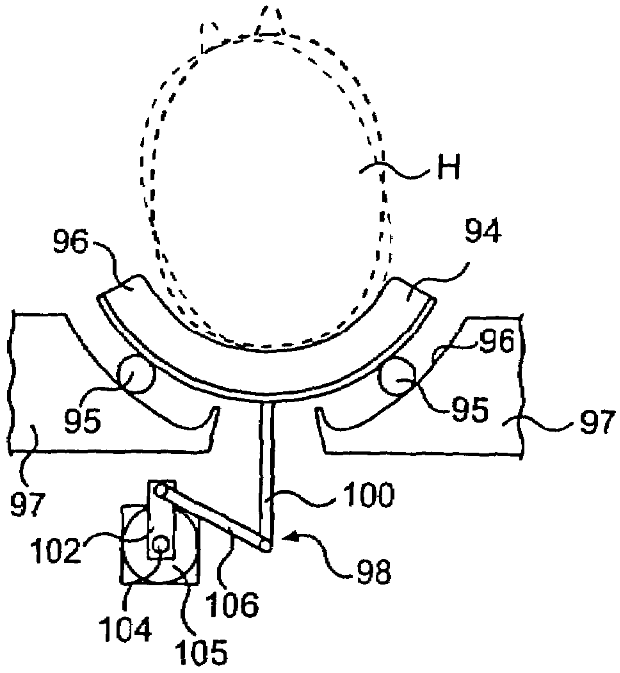
FIG. 21 PRIOR ART
FIG. 21 is an end elevational view of a cervical rotation apparatus in accordance with a further embodiment of U.S. Pat. No. 6,692,451.

Referring now to FIG. 21, a further embodiment of U.S. Pat. No. 6,692,451 is shown which is used in providing movement of the head of a user, viz., in providing rotation of the neck or cervix. A cervical support member 94 of a shallow U-shape is used to support the head and neck. Member 94 is supported by, and rolls on, roller bearings 95 which are, in turn, supported in bearing races 96 defined by spaced supports 97. Rotational movement of support member 94 take place under the control of a control mechanism 98. Control mechanism 98 includes a link or arm 100 rigidly affixed to support member 94, a drive or control arm 102 connected to the motor drive shaft 104 of a motor 105 and a linking arm 106 pivotably connected to arms 100 and 102. Control mechanism 98 produces limited rotation of support member 94 so as to gently rotate and exercise the neck.

Figure 22:
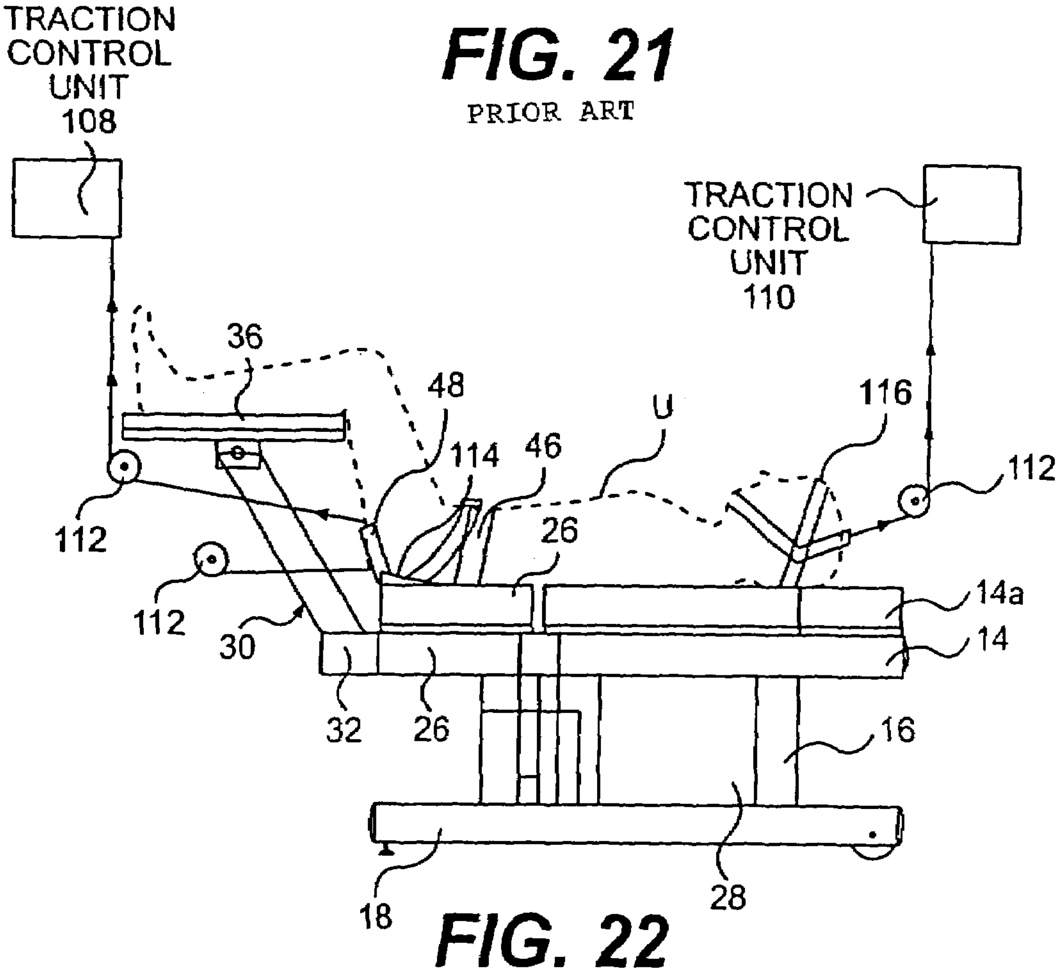
FIG. 22 PRIOR ART
FIG. 22 is a side elevational view of a further modified form of the apparatus of FIG. 1, providing the addition of traction.

Turning to FIG. 22, an embodiment of U.S. Pat. No. 6,692,451 is shown which basically corresponds to that of FIG. 6 and FIGS. 9, 10 but includes a traction arrangement for keeping a user U in traction during the passive movements provided by the device 10 (in this case, movement of the lower trunk and legs). It will, of course, be appreciated that traction can also be provided with other embodiments described above and that other traction arrangements can be used as well. In FIG. 22, both a lumbar traction control device 108 and a cervical traction control 110 are provided. As indicated schematically in FIG. 22, suitable pulleys 112, and separate harnesses 114 and 116 are provided in providing the traction desired.

The passive range of motion control provided by device 10 can be provided on continuous duty basis, with low maintenance requirements and the need for only very occasional lubrication. The mechanisms used afford a very smooth operation, and linear actuators employed preferably have a stroke length of about 5" or 6". The force exerted is preferably no greater than about 50 lbs.

The control unit 28 is adapted to provide push button programmable motion, and is preferably programmable to nine ranges of motion as follows (in degrees): 10-7½-5-2½-0-2½-5-7½-10. The timer used is also programmable, preferably from fifteen minutes to eight hours, and is set to automatically return to zero when the timer times out.

The frame construction of at least the embodiments described above permits the apparatus to be stood on end for storage in a closet or other small area.

The control unit 28 preferably includes an A/B switch or other switching device (not shown) for switching between the linear actuator control (shown, e.g., in FIGS. 5 and 6) and the pneumatic pump control (FIGS. 15, 16 and 17, 18).

Figure 23:
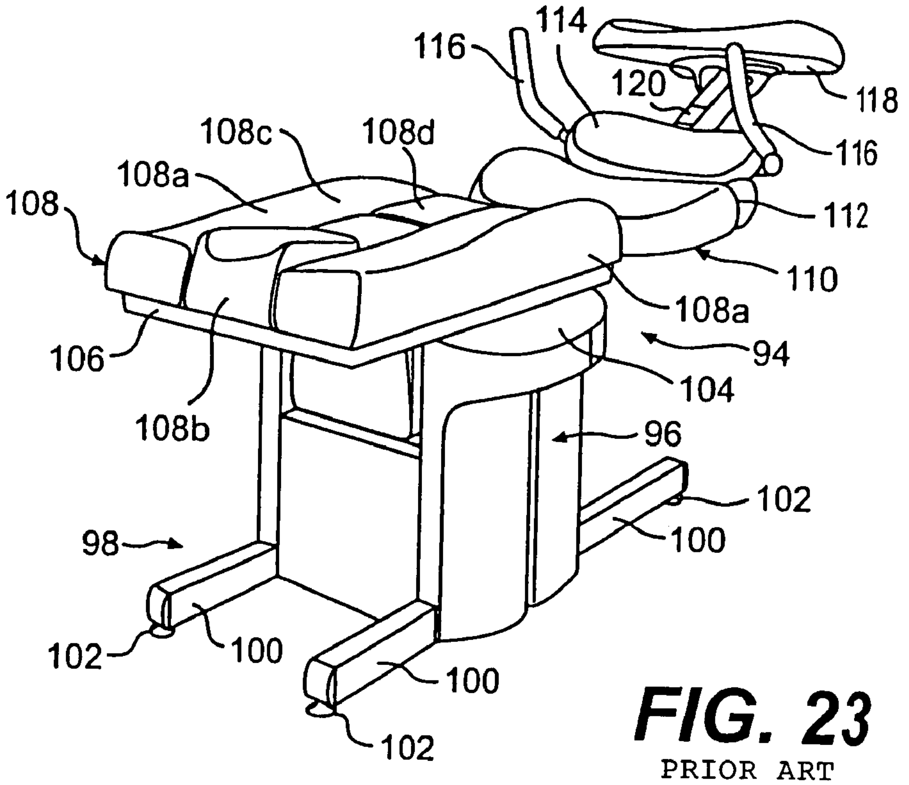
FIG. 23 PRIOR ART
FIG. 23 is a perspective view of the passive range of motion exercise and/or treatment apparatus according to a further embodiment of U.S. Pat. No. 6,692,451.
Figure 24:
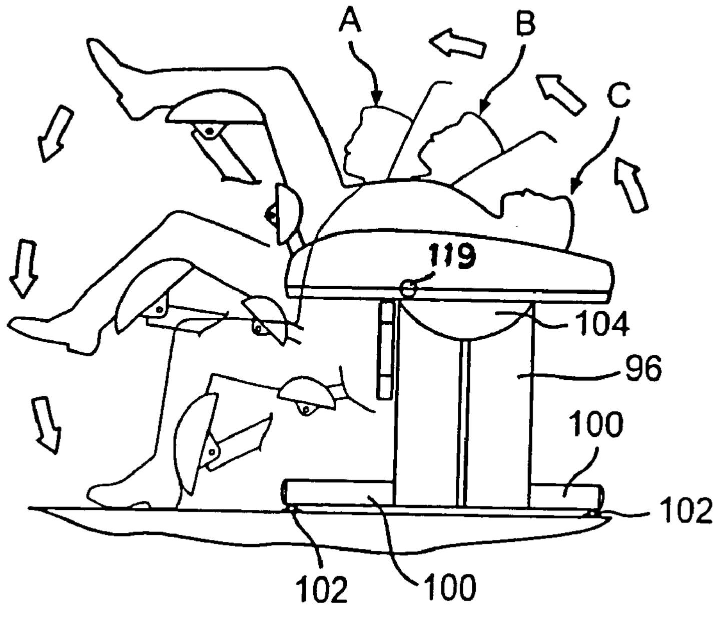
FIG. 24 PRIOR ART
FIG. 24 is a side elevational view of the apparatus of FIG. 23, with parts omitted, illustrating an automated reclining feature thereof.

Referring to FIGS. 23 and 24, there is shown a further embodiment of U.S. Pat. No. 6,692,451 which is particularly adapted for clinical use. This embodiment is similar to that of FIG. 1 but there are both major and minor differences. The apparatus, which is generally denoted 94, includes a base cabinet 96 and a base 98 formed by two pairs of horizontally extending support legs 100 extending outwardly from cabinet 96 on opposite sides thereof. Levelers 102, corresponding to those described above, are provided at the free ends of support legs 100. A control unit including an external control panel or controls indicated at 104 is housed within cabinet 96. The overall height of apparatus 94 is greater than that of the apparatus of FIG. 1 for reasons which will become apparent.

The apparatus 94 includes a first (table) support member 106 which is similar to that described above and which has seated thereon a body support pad or cushion arrangement 108. In the embodiment illustrated, the latter includes a pair of spaced, laterally disposed contoured pads 108*a*, and a central head rest 108*b* in alignment with a pair of heating and/or cooling units 108*c*, all as described previously.

A second support member 110 is pivotably connected to support member 106 and is controllably pivoted relative thereto, as described above, under the control of control panel 104. Support member 110 includes a contoured covering pad or cushion 112 seated thereon, and affixed thereto, as shown.

A further, separate seat member 114 is affixed to second support member 110 and moves therewith. As shown in FIG. 23, seat member 114 may include laterally disposed, outwardly extending arms 116 at opposite sides thereof which are adapted to be gripped by a user.

A lower leg (calf) support member 118 is affixed to seat member 114 by a support strut 120 and is pivoted in a self-adjusting manner with respect to strut 120, as was described above in connection with FIG. 1 and the related drawing figures.

An important feature of the embodiment of FIGS. 23 and 24 is that, in this embodiment, a reclining functionality is provided wherein, in use of the apparatus 94, the user is first seated on the apparatus or machine in an upright seated position and is then reclined, i.e., passively moved to a reclining 90/90 position, without any effort on his or her part. It will be appreciated that this feature can be of substantial importance in dealing with a seriously ill or infirmed person in that the person does not have to climb onto the machine or be placed on the machine, thereby avoiding stresses that might ordinarily occur with such placement. The first support member 106, second support member 110, seat member 114, and leg support 118 all form a unitary body support unit or construction that is pivotable with respect to base cabinet 96 about a horizontal pivot axis indicated at 119. (In FIG. 24, a single seat member 114, which is disposed at a right angle with respect to first support member 106, replaces members 110 and 114 of FIG. 23, for purposes of simplicity.) With the provision of such a pivotable unitary construction, it will be appreciated that, referring to FIG. 24, by effecting simple pivoting of this unitary construction or unit about the horizontal pivot point 119, a user can be moved from the position indicated at A in FIG. 24 wherein the user is seated on seat member 114 with the backs of the lower portions of his or her legs against leg support 118, and his or her back against first support member 106, through an intermediate position, indicated at B, to a final inclined, "90/90" treatment position, indicated at C, wherein the back of the user rests on support member 106, his or her buttocks abut against seat member 114 and the legs rest on leg support 118. Thus, the entire body support (including the linkage mechanism (not shown) which provides the relative lateral pivoting between sections of the body support as described above) pivots or tilts through 90° relative to the base cabinet 96 and base support 98, which remain stationary.

The description thus far has been of the passive motion apparatus or machine of U.S. Pat. No. 6,692,451, and as indicated above, this apparatus represents a major advance which is capable of providing a number of different continuous passive motions. The present invention is concerned, inter alia, with four of the most important motions to be provided, two rotational motions and two bending motions, viz., cervical rotation, cervical bending, lumbar rotation and lumbar bending. Embodiments of the present invention will now be described which provide these motions individually as well as provide for combining of the motions. In addition, these embodiments of the invention provide for other movements including tilting of the cervical and lumbar sections. Moreover, these embodiments include a number of other important features as will be discussed below or will be apparent.

Figure 25:
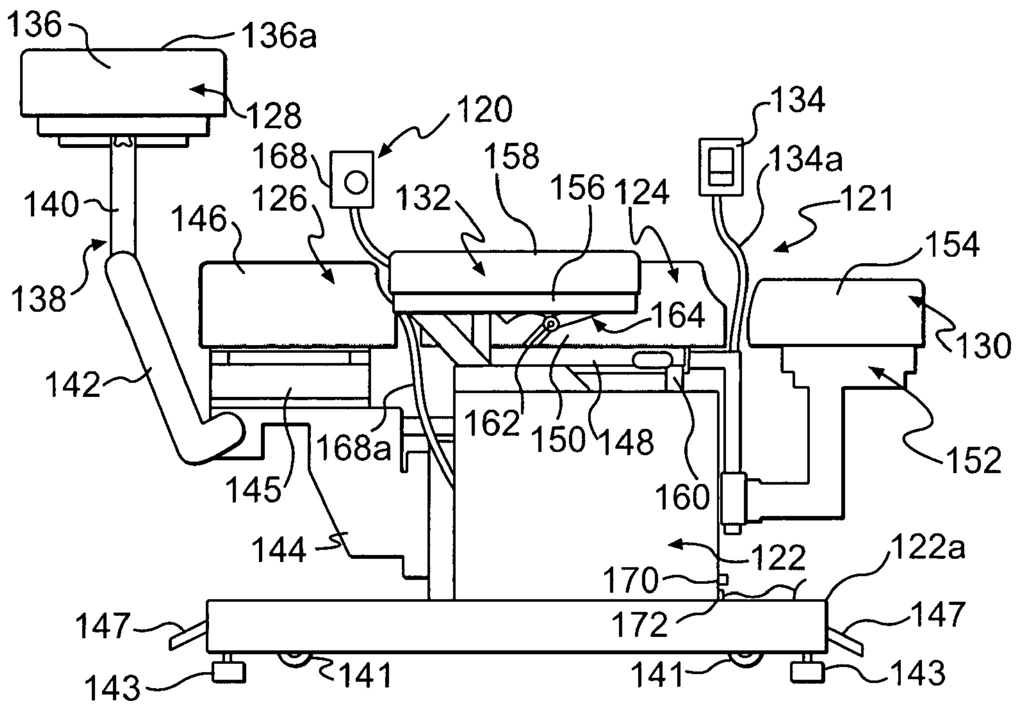
FIG. 25 is a schematic side elevational view of a continuous passive motion apparatus in accordance with a preferred embodiment of the present invention, shown in the reclined position or configuration with the calf support assembly elevated.
Figure 27:
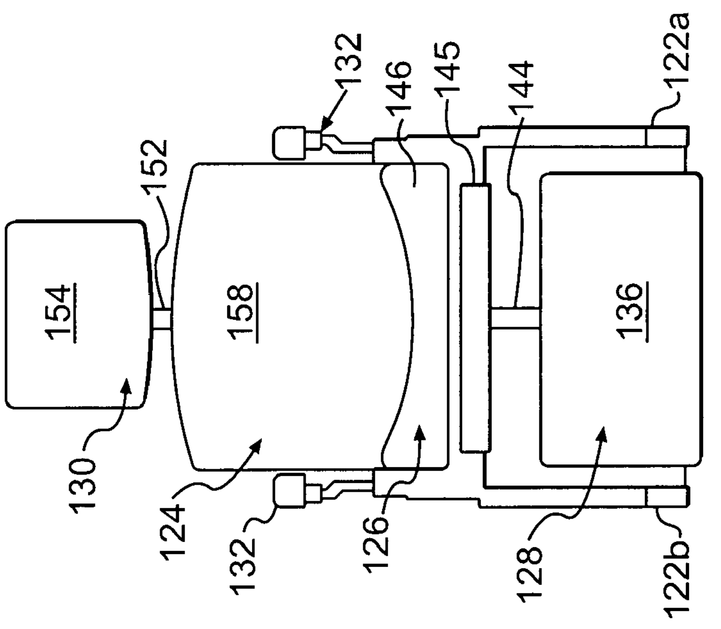
FIG. 27 is a simplified front elevational view of the apparatus of FIG. 25, in the position shown in FIG. 26.

Referring to FIGS. 25 and 27, a preferred embodiment in accordance with the present invention is illustrated. As shown in FIG. 25, the device or apparatus, which is generally denoted 120, includes, as the major components thereof, a base or housing 122 which houses a computerized control system (not shown) and is supported by a pair of support rails 122*a* and 122*b*, a recline table or backrest section 124, a lumbar or pelvis support section 126, a calf or lower leg support section 128, a cervical support section 130, an armrest assembly 132 and a part of the aforementioned control system represented in FIG. 25 by a palmtop computer or controller device 134. The lumbar support section 126, the backrest section 124 and the cervical support section together form what is referred to below as a treatment table, which is generally denoted 121 in FIG. 25.

As can be best seen in FIG. 25, calf support section 128 includes a cushion or an upholstered support member 136 having an upper surface 136*a* on which, in use, the calves of a user rest in side by side relation. Support member 136 is connected to lumbar support section 126 by an articulated linkage 138. The latter which enables the positioning of support member 136 relative to the rest of the apparatus 120 to be varied so as to accommodate users of different heights and also permits support member 136 to be partially stowed beneath the lumbar support section 126 in an initial set-up mode, shown in FIGS. 26 and 27 and described in more detail below, in which the apparatus 120 is caused to assume a generally L-shaped chair-like configuration with the user or patient initially seated on lumbar support section 126 and with the sections 124 and 130 serving as a backrest and headrest, respectively.

The articulated linkage 138 includes a first link arm 140, connected to calf support section 128 and a second link arm 142 pivotably connected to a support member 144 for lumbar support section 126 and pivotably connected to first link arm 140. The articulated linkage 138 is constructed such that the support section 128 is releasably fixed in the position to which it is moved and in a preferred embodiment, includes a conventional releasable locking mechanism (not shown) for retaining the calf support section 128 in the selected position and/or for retaining the calf support section in the stowed position shown, e.g., in FIG. 26.

It is noted that while the calf support section 128 can be moved manually between the various positions described above and also discussed below, i.e., between a stowed position, a position level with the remainder of the treatment table 121, and a raised position, in a preferred embodiment, this movement is motorized. In one preferred embodiment, three separate motors (not shown) are used to effect the necessary movements. Any conventional motor drive arrangement can be used that will effect the necessary movements of the calf support member 136 and articulated linkage 138 between the various positions described above and, in general, in the one preferred embodiment mentioned above, a separate motor and a corresponding motor driven linkage (not shown) is used to effect each motion. Again, this can also be done manually but the motorized embodiment is generally preferred because it is easier for the caregiver or other user.

The apparatus or machine 120 further includes four support rollers or casters 141 mounted on rails 122*a* and 122*b* as well as four adjustable leveling pads 143 (two of which are shown in FIG. 25) and four associated control levers 147 (two of which are shown in FIG. 25). These features as described in more detail below in connection with FIGS. 40 and 41.

Lumbar support section or unit 126 includes a base support member 145 which is affixed to support member 144 and which supports a cushion 146.

Similarly, backrest or recline section 124 includes a base support member 148 which supports a cushion 150, while cervical support section 130 includes a L-shaped support member indicated generally at 152, that supports a cushion 154, and each armrest or arm support assembly 132 includes support member 156 which supports an armrest cushion 158.

Figure 26:
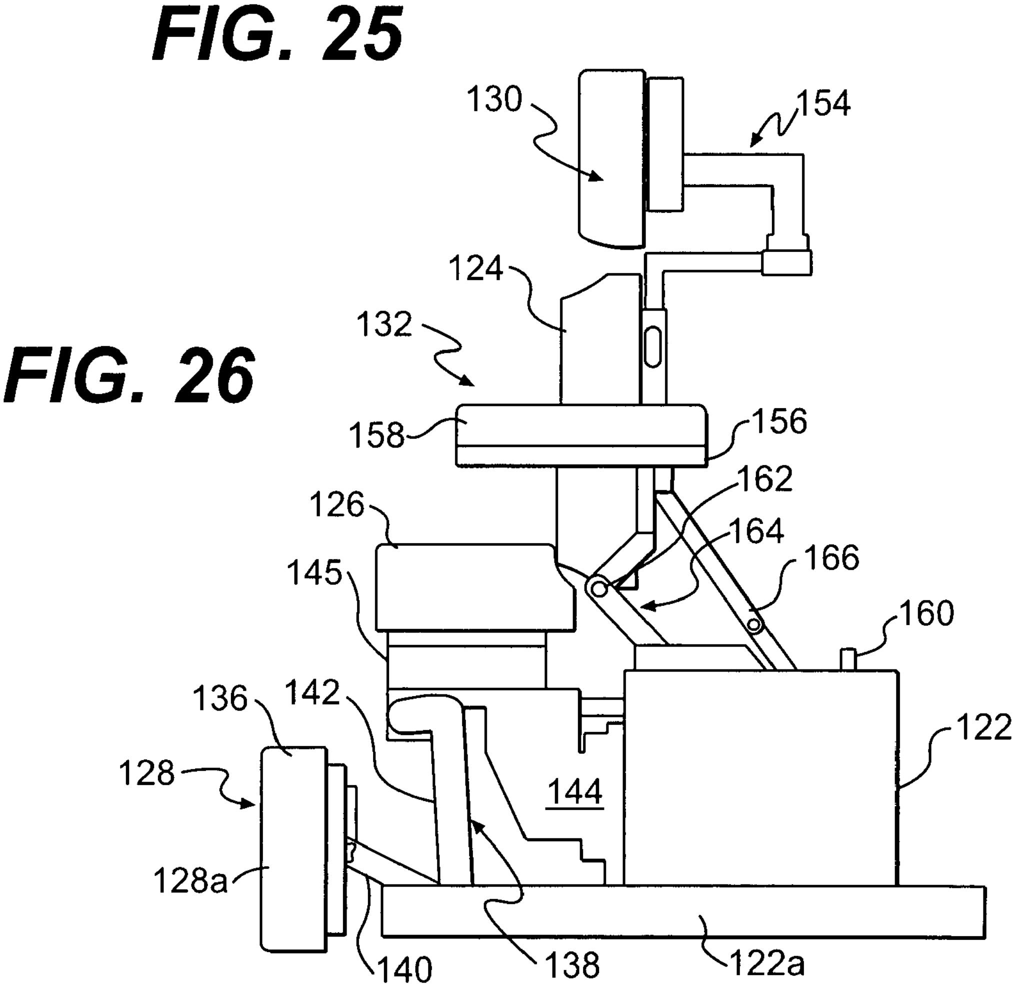
FIG. 26 is a side elevational view of the apparatus of FIG. 25, shown in the upright position or configuration with the calf support assembly stowed, and wherein parts have been omitted for purposes of clarity.

As is perhaps best seen in FIG. 26, a rest or stop 160 for backrest unit or recline table 124 is mounted on, or supported on, base 122. A recline linkage 164 including a pivot point 162 is also mounted on base 122 along with articulated recline levers 166 which project out of base 122 and are controlled by a DC motor (not shown) to raise and lower backrest support section 124 and cervical support section 130 between the positions shown in FIGS. 25 and 26. Recline linkage 164 provides pivoting movement of armrest assembly 132 between the lowered horizontal position shown in FIG. 25 (and FIG. 28) and the raised horizontal position shown in FIGS. 26 and 27, while, as stated, recline levers serve to move backrest section 124 and associated cervical section 130 between the position shown in FIGS. 26 and 27 and the position shown in FIG. 25 (and FIG. 28).

As is shown in FIG. 25 (but is omitted in FIGS. 26 and 27), a patient controlled remote stop button or kill switch 168 is connected by cable 168*a* to the aforementioned computerized controller (not shown) located within base 122 while a power switch 170 is mounted on base 122 and a power cord connector 172 and associated power cord 172*a* (see also FIGS. 40 and 41) connects the computerized controller (not shown) to a suitable power source, e.g., a wall outlet (not shown).

Figure 28:
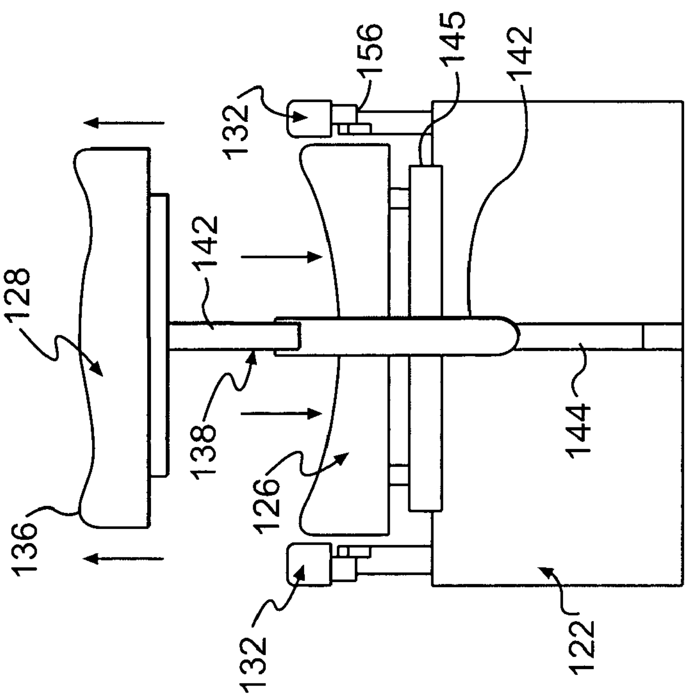
FIG. 28 is a simplified front elevational view of the apparatus of FIG. 25.

Referring to FIG. 28, a simplified end view of the device or machine 120 is shown, wherein, in use, the patient would be supported generally horizontally, with his/her arms on the armrest cushions 156 and with higher lumbar region supported in lumbar cushion 146. Calf rest cushion 136 of calf rest section or unit 128 is shown in the elevated portion thereof. As indicated above, the articulated support assembly 138 enables the legs of a patient to be manually placed at a selected height and to be also moved axially relative to lumbar section 126, thereby enabling the legs to be positioned at different elevations in a comfortable position which accommodates the particular physical characteristics of a patient.

Figure 29:
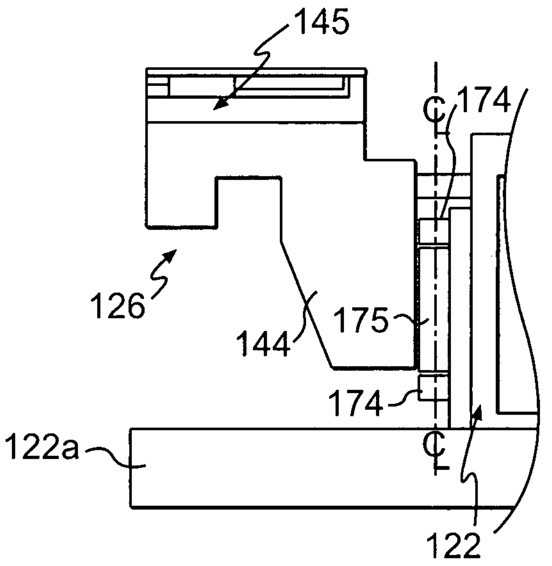
FIG. 29 is a simplified side elevational view partially broken away, showing, in more detail, the lumbar section of the apparatus of FIG. 25.

FIG. 29 shows a portion of the lumbar section or unit 126 with the cushions, covers and hardware removed for purposes of clarity. The lumbar support subassembly 145 pivots on support member 144 which is pivotably mounted on base or base frame 122 by a pair of vertically spaced blocks 174 which support a two part pivot shaft 175 formed integrally with support 144 so as to provide side bending of the lumbar region of a patient.

Figure 30:
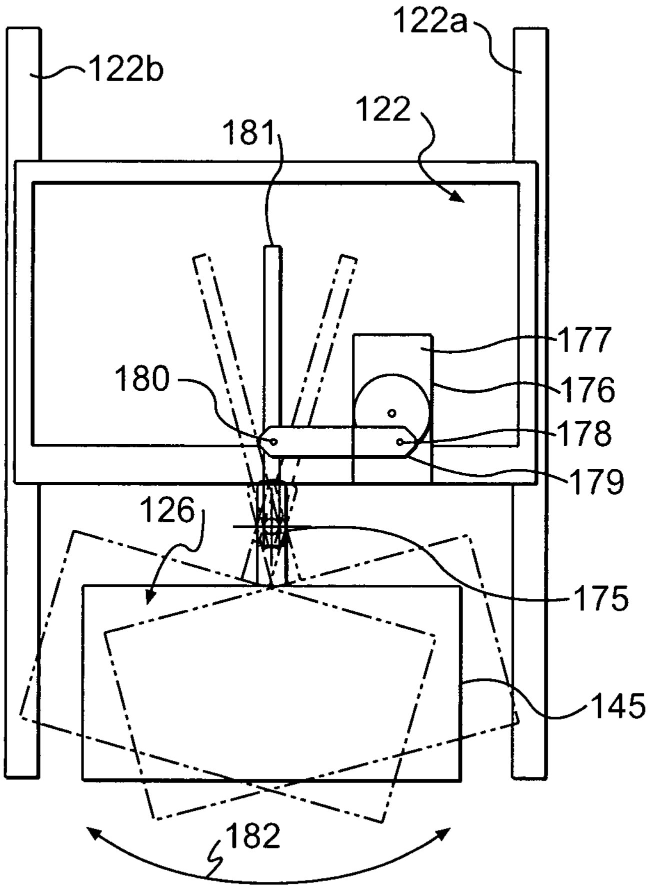
FIG. 30 is a simplified bottom plan view of the side bending drive arrangement for the lumbar section of FIG. 25.

The drive arrangement for this side bending motion is shown in FIG. 30 wherein a belt-driven transmission 176 rotates a gear 177 which is attached by a pivot pin 178 to a side bending link 179. Link 179 is attached by a further pivot pin 180 to drive link 181 affixed to pivot shaft 175. Thus, rotation of gear 177 causes a pivoting, side bending movement, indicated by double headed arrow 182, of lumbar section 126 about vertical shaft 175 between the lateral end positions shown in FIG. 30. The side bending movement typically takes place in a horizontal plane although the lumbar section 126 can be tilted as mentioned above and described below.

Figure 31:
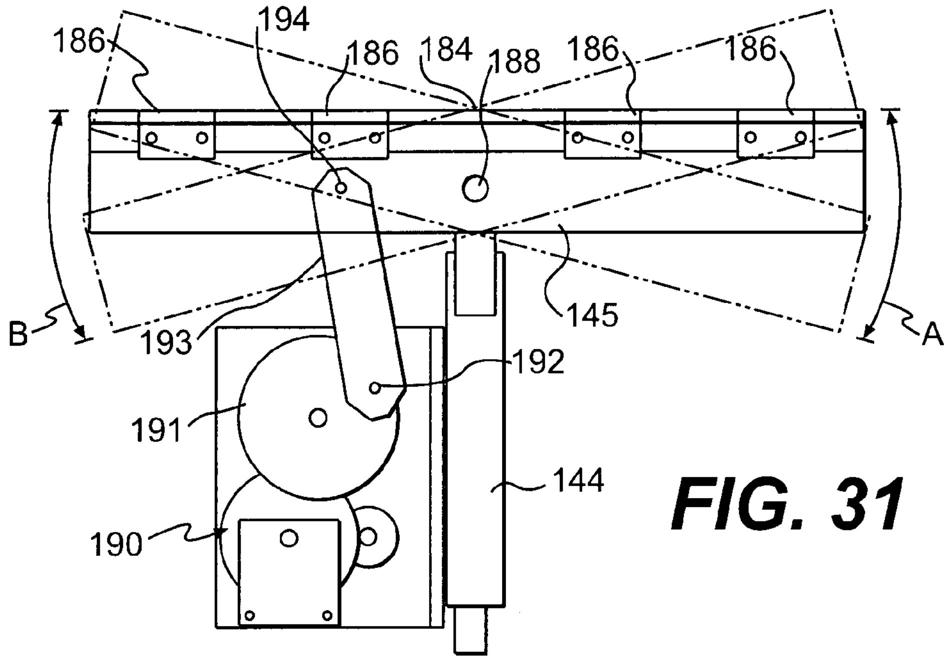
FIG. 31 is a simplified end elevational view showing the rotational drive arrangement for the lumbar section of FIG. 25.

Referring to FIG. 31, there is shown the apparatus for providing rotation of the lumbar region of patient, again with all cushions, covers, guards and hardware removed for purposes of clarity. A lumbar cushion support 184 is pivotably mounted on support frame or member 145 by a series of hinges 186. Lumbar section or unit 126 pivots about a shaft 188 which typically extends horizontally. A belt-drive transmission with an associated micro-stepping motor is indicated at 190 and the belt-drive drives a gear 191 pivotably connected by a pivot pin 192 to a link 193 which converts the angular rotation of gear 191 into linear motion. To this end, link 193 is connected is connected by a further pivot pin 194 to the lumbar support or frame 145. Thus, rotation of gear 191 by motorized drive 190 causes rotation of lumbar support 145 about pivot shaft 188 between the positions shown in dashed lines in FIG. 31. As discussed below, this motion can be controlled to, for example, limit the lumbar rotation to that shown by arrow A or that shown by arrow B, among other options.

Figure 32:
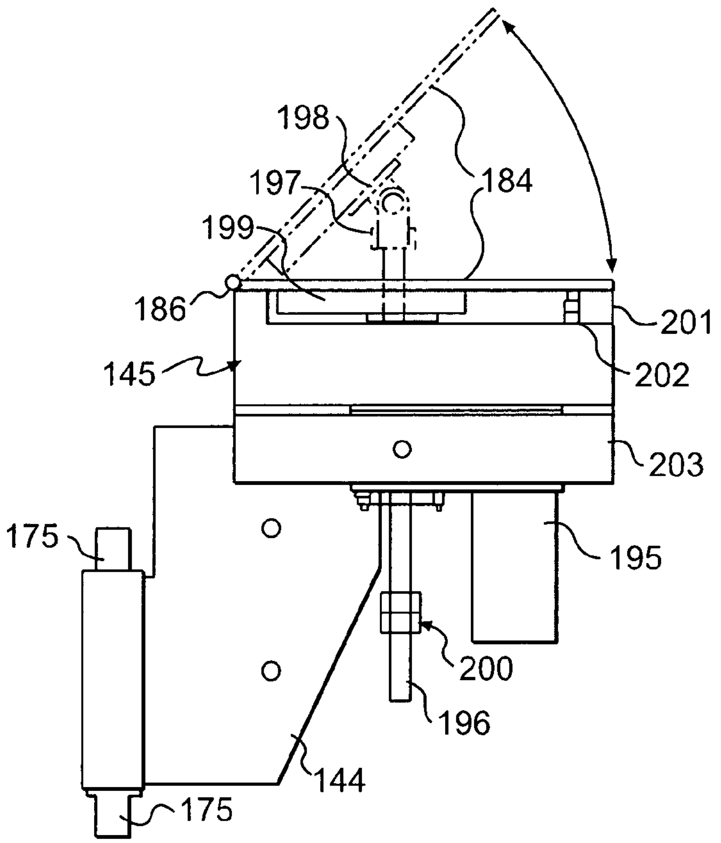
FIG. 32 is a simplified side elevational view, taken on the opposite side from FIG. 25, showing the tilt drive arrangement for the lumbar section of FIG. 25.

Referring to FIG. 32 (which is taken from the opposite side of FIG. 25), there is illustrated a tilt mechanism or apparatus for lumbar section 126. The lumbar cushion support plate 184 is normally horizontal as shown in solid lines but is movable to the position shown in dashed lines by an arrangement including a DC motor and transmission unit, indicated at 195, which drives a threaded rod 196 which is connected at one end to a lumbar sagittal tilt threaded rod bracket 197. Bracket 197 is, in turn, pivotably connected to a lumbar sagittal tilt actuation bracket 198 affixed to a lumbar cushion strength plate 199 secured to support plate 184.

A nut and lock nut combination indicated at 200 limits the travel of rod 196 and thus the amount of upward tilt of plate 184.

Stop blocks 201 abut lumbar cushion mount plate 184 in the rest (e.g., horizontal) position, and a position switch 202 limits lowering of plate 184 by switching off motor and transmission unit 195 when plate 184 comes into contact with switch 202.

As shown in FIG. 32, lumbar support frame 145 includes a lower motor mount frame 203 on which the motor and transmission unit 195 described above are mounted.

In generally, motor and transmission 195, when activated, produces linear travel of threaded rod 196 which is converted into tilting movement of cushion support plate 184 so that the lumbar region of a patient can be tilted as desired.

Figure 33:
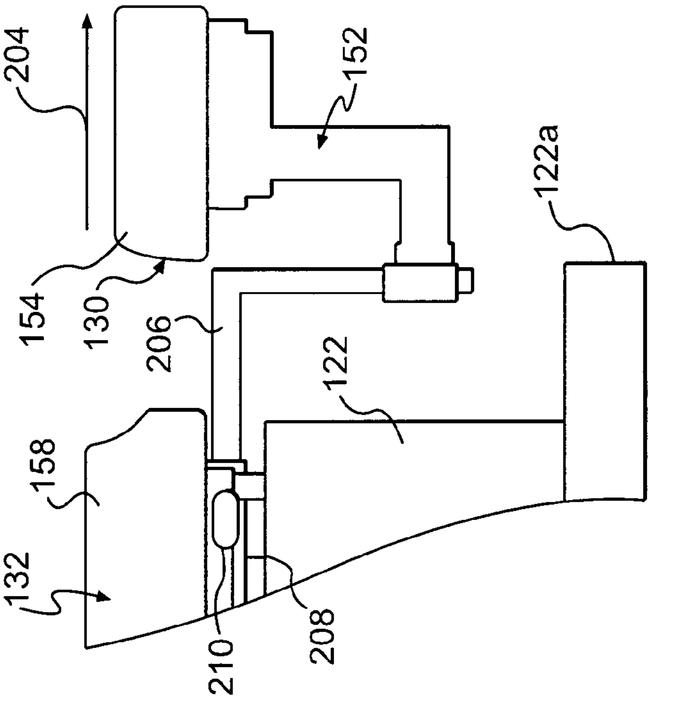
FIG. 33 is a simplified side elevational view, partially broken away, showing the extension arrangement for the cervical section of the embodiment of FIG. 25.

Turning now to the cervical motions provided, and referring first to FIG. 33, as indicated by arrow 204, cervical support section or unit 130 can be moved linearly with respect to backrest section 124 so as to accommodate patients of different heights. To this end, the cervical support member or frame 156 is affixed to a further L-shaped frame element 206 which is slidable in a slide tube 208 mounted in backrest support member 148 or otherwise mounted on base 122. A T-shaped locking handle 210 with an associated locking pin (not shown) adapted to be inserted into one of a linear series of adjustment holes (not shown) is used to establish and fix the longitudinal position of cervical section 130 so as to provide stability. A similar locking arrangement is described in more detail below in connection with FIG. 38.

Figure 34:
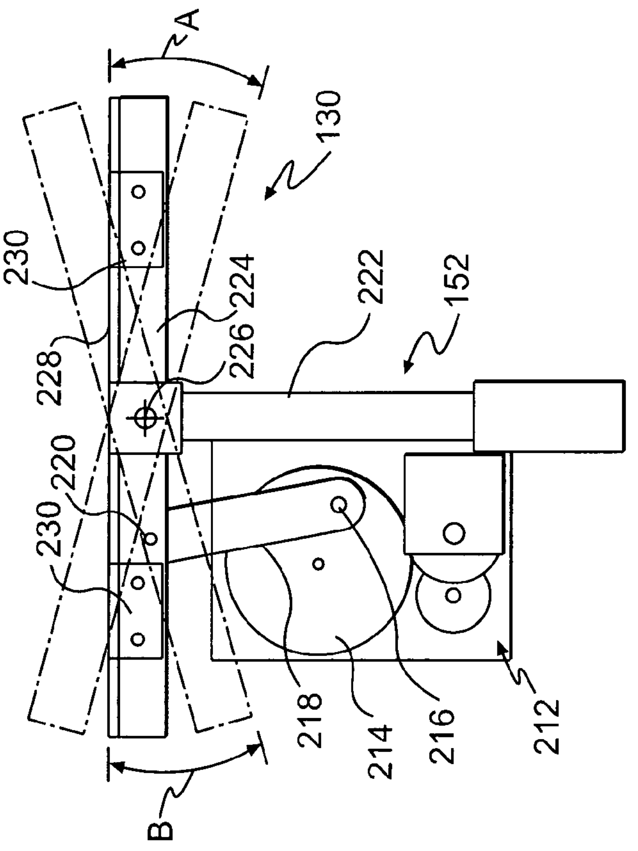
FIG. 34 is a simplified end elevational view similar to that of FIG. 31 showing the rotational drive arrangement for the cervical section of FIG. 25.

Referring to FIG. 34, an arrangement for providing cervical rotational motion is illustrated. The arrangement is similar to that for lumbar rotation and unit comprising a belt-drive transmission with a micro-stepping motor, indicated at 212 is used to drive a rotary gear 214 which is connected by a pivot pin 216 to a link 218. The latter is, in turn, connected by a pivot pin 220 to the cervical support or frame 152. As illustrated, frame 152 includes a vertically extending frame support 222, and a support member 224 pivotably connected thereto by a pivot shaft 226. Thus, as pin 216 rotates with gear 214, support member 224 is caused to rotate around pivot shaft 226 as is indicated in dashed lines in FIG. 34.

A cushion support plate 228 is pivotably connected to support member 224 by hinges 230 so as to enable a tilting action described below to be carried out.

Figure 35:
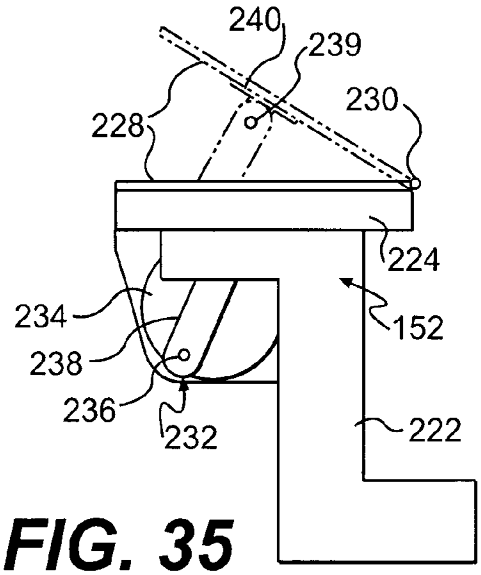
FIG. 35 is a simplified side elevational view, similar to FIG. 32 and taken from the opposite side from FIG. 25, showing the tilt arrangement for the cervical section of FIG. 25.

Referring to FIG. 35, the arrangement for effecting this tilting action is shown (from the right hand side as viewed in FIG. 25 so that support frame 152 faces in the opposite direction). A unit comprising belt-drive transmission with a micro-stepping motor, indicated generally at 232, provides the drive for the sagittal tilt action and, more specifically, drives a rotating gear 234 which is connected by a pin 236 to one end of a link 238. The latter is pivotably connected at the opposite end by pin 239 to a bracket 240 (shown in dashed lines) secured to cervical cushion mounting plate 228.

With this arrangement, rotation of gear 234 causes link 236 to raise and lower, i.e., tilt plate 228 so as to provide sagittal tilt, i.e., to vary the tilt angle at which the head and neck are supported. Thus, when the plate 228 is raised, the chin of the patient is inclined toward the torso.

Figure 36:
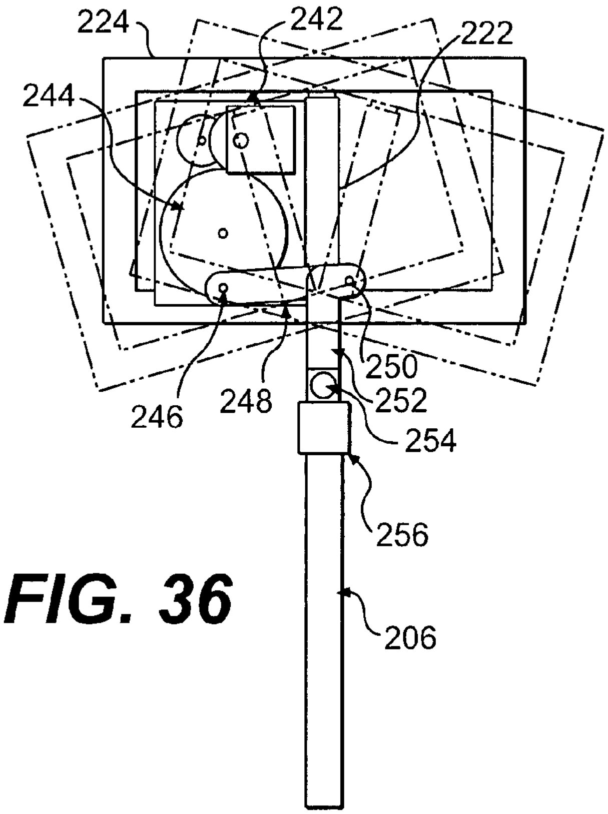
FIG. 36 is a simplified bottom plan view, similar to that of FIG. 30, showing the side bending drive arrangement for the cervical section of FIG. 25.
Figure 37:
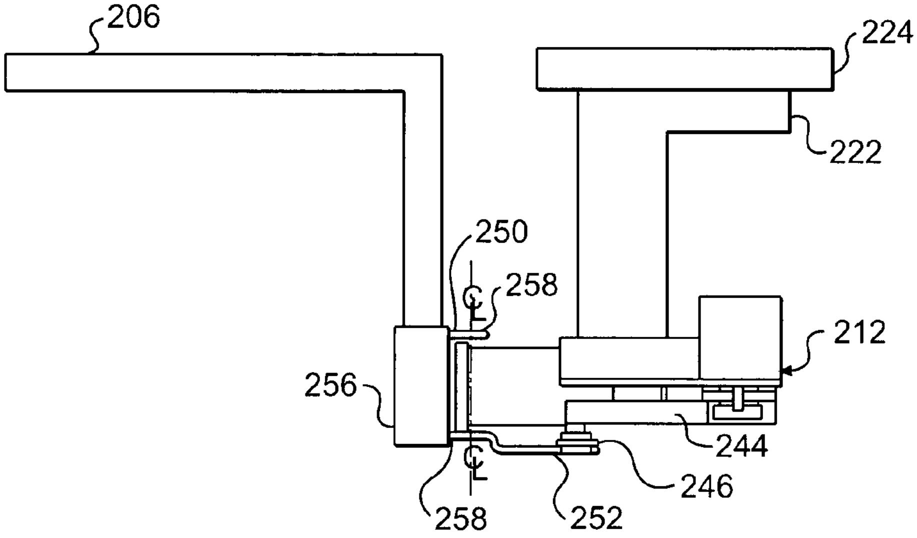
FIG. 37 is a simplified side elevational view of a portion of the cervical section of FIG. 25, also showing the side bending drive arrangement.

Turning to FIGS. 36 and 37, cervical side bending will now be described in connection with these figures. Referring to FIG. 36, there is shown a simplified bottom view of the arrangement for providing cervical side bending. In the rest position shown in solid lines, the sides of support frame 224 extend generally parallel to the sides of the machine 120, i.e., parallel to the longitudinal axis of the machine, and the neck of the patient would extend along this axis. Side bending is effected by a motorized belt-driven transmission unit, indicated generally at 242, which drives a rotating gear 244 connected by a pivot pin 246 to a link 248. The latter is pivotably connected by pivot pin 250 to a fixed or stationary link mount 252. Link 252 is fixed to the support member 206 which was mentioned above and which is received in tube 208 (see FIG. 33) of backrest section 132. Link mount 252 is fixedly mounted relative to a vertical cervical side bending pivot shaft 254. A travel car 256, which is described in more detail below in connection with FIG. 38, is indicated at 260.

FIG. 37 is a side elevation view showing the pivotable connection of support frame 222 to pivot shaft 250 and the location of the drive transmission with micro-stepping motor unit 212 relative to the frame support members 222 and 224 as well as the location and configuration of the side bending link 248 and stationary mount link 252. The moving portion of cervical subassembly pivots on the pivot shaft 254 which is welded through means of tabs 258 to travel car 256.

It will be appreciated from the foregoing description that rotation of gear 244 causes link 248 to move relative to fixed link mount 252 and thus causes angular movement, about pivot shaft 250, of support frame 224 (and thus cervical unit 130) between the positions shown in dashed lines in FIG. 36.

Referring to FIG. 38, there is shown in more detail the mechanism or arrangement of raising and lowering the cervical unit or section 130, with other parts omitted for purpose of clarity. As indicated above, support member 222 of support frame 152 is connected to support element 206 and, more particularly, is affixed to a downwardly depending leg 206*a* of L-shaped support element 206 by the travel car or movable connector member 256. Travel car 256 includes rollers (not shown) which enable movement thereof along leg 206. A linear series of adjustment holes 260 provided in leg 206*a* cooperate with a spring loaded pin (not shown) of a T-shaped handle or T-handle 262 to clamp or lock travel car 256 in a selected fixed position along leg 206*a* and thus fix the position of cervical support member or frame 152 and correspondingly fix the position of cervical unit 130.

FIG. 39 is a front elevational view of one embodiment of the palmtop computer or controller 134. The controller 134 is generally conventional and includes a power switch 134*a*, a display area or screen 134*c*, a home icon 134*d*, application icons 134*e*, a navigator 134*f* and application buttons 134*g*, and is connected by computer cable 134*a* to the computer (not shown) housed within base 122.

It is important to note that although in the exemplary embodiment under consideration, a handheld controller is used, in accordance with a further preferred embodiment, controller 134 can be dispensed with and the base computer (not shown) can be pre-programmed to provide the desired motions, as well as a schedule of such motions. In this regard, in accordance with one implementation of this embodiment, a card containing a patient's treatment regime can simply be plugged into the computer, and the computer can also be used to monitor the progress of the patient through his or her treatments. This particular embodiment is preferred for some applications and in this embodiment, the computer (not shown) housed in base 122 is preferably interfaced by the user through a graphical touch screen (not shown) which enables the desired therapy to be programmed in a manner similar to that described below for palmtop computer 134. Warnings and other notifications are provided on the screen to alert the user to potential dangers and to provide other information. More generally, the various motors described above are all preferably computer controlled, and are programmed as described below with specific sequences in order to carry out the desired treatment or therapy. As is also described below, each motor is independently controlled or sequenced by the computer with respect to motion limits, speeds and repetitions programmed by the user.

Figure 40:
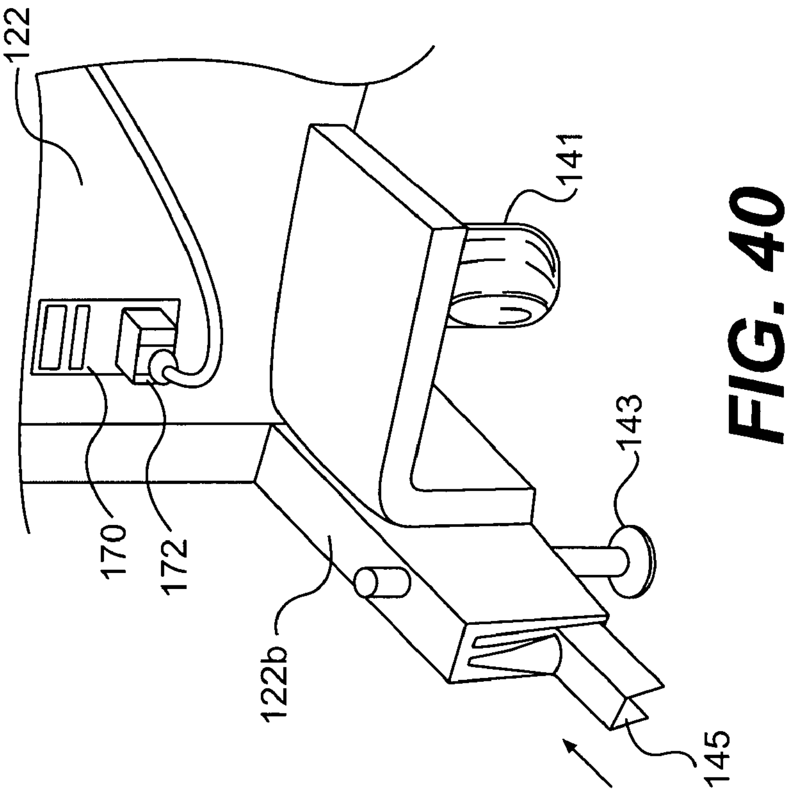
FIGS. 40 and 41 are perspective views of the leveling pad arrangement of FIG. 25, showing the locking and releasing or re-extending operations, respectively.
Figure 41:
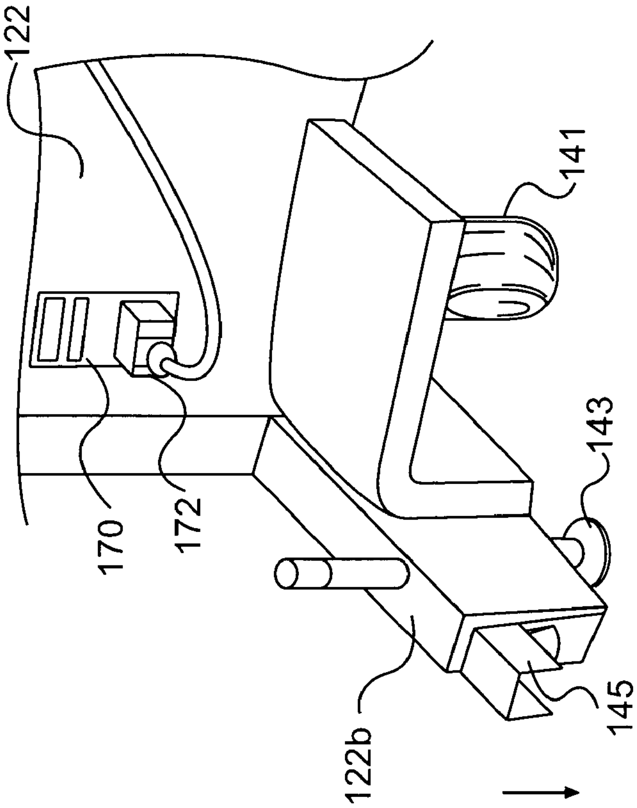

Referring to FIGS. 40 and 41, there is shown the leveling pad arrangement mentioned above in connection with FIG. 25. Rollers 141 are provided to enable the overall apparatus or machine 120 to be moved as needed. Leveling pads 143 are provided to fix the position of the machine 120 when the machine 120 is in use, and to ensure that machine 120 is level. A leveling pad 143 is released by firmly tapping on an associated lever 147 as indicated in FIG. 40, and can be re-extended by pressing down on lever 147 as indicated in FIG. 41. The lever mechanism (not shown) includes a biasing spring (not shown) and acts in the manner of a jack to enable raising and lowering of the associated pad 143. A leveling pad 143 can be adjusted by rotating the pad in one direction to extend the pad and in the opposite direction to retract the pad. A pad 143 can only be adjusted when the pad mechanism is released (FIG. 41). Although this arrangement is advantageous, other adjustment or leveling mechanisms can, of course, be used.

Turning to a consideration of the set-up operation, i.e., to steps taken in preparing the apparatus or system for a treatment, before a patient is placed on the treatment table 121 formed by support members 124, 126 and 130, as an initial step, the calf support unit 128 is preferably lowered so as to be partially stowed under lumbar support member 126 as shown in FIGS. 26 and 27.

A check is also made to make certain that the treatment table 121 is level and is supported by the four leveling pads 143. Suitable adjustments of pads 143 can be made, as necessary, as described above in connection with FIGS. 39 and 41.

If necessary, the treatment power switch 170 is turned and, also, if necessary, the power switch 134*b* of the palmtop computer 134 is turned on.

Figure 42:
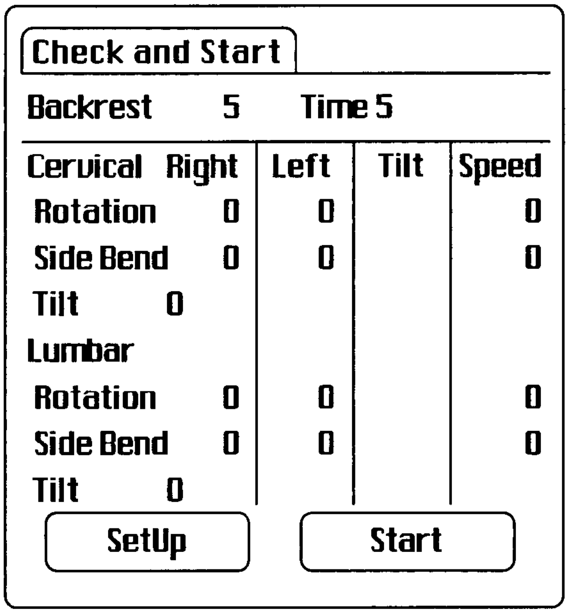
FIGS. 42 to 49 are front elevational views of the screens or menus used in selecting and entering different modes of operation of the apparatus of FIG. 25.
Figure 43:
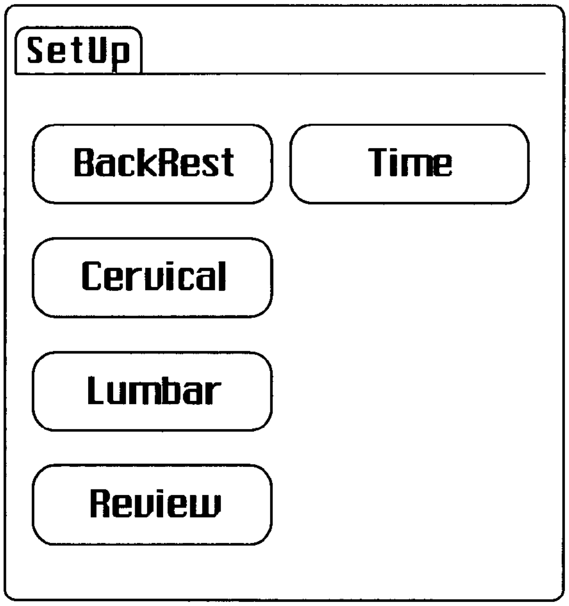

The "Check and Start" screen shown in FIG. 42 is then checked. If desired, based on the condition of the patient, treatment table 121 can be raised to the seated position shown in FIGS. 26 and 27. This can be done automatically using the palmtop computer 134 by selecting "Setup" so that the "Setup" screen shown in FIG. 43 is displayed, selecting "Backrest" so that the "Back" menu shown in FIG. 42 is displayed and then selecting "Full up" and "Enter." The treatment table 121 is then automatically raised to the seated position. It is noted that it may not be advisable to position the patient in this manner because, e.g., of medical reasons, and the decision is, of course, up to the practitioner.

If necessary, preliminary adjustment can be made to the height and extension of the cervical support 130 as described above.

With this preliminary preparation for operation, the patient can be positioned on the treatment table 121. To so position the patient, the patient is first seated, or reclined, on the treatment table 121. The cervical support extension arrangement including support element 206 and cooperating tube 208 (see FIG. 33) for cervical support member 130 is manually adjusted to match the height of the patient as described above. The cervical support height is also adjusted to the desired position so that cervical support member 130 contacts the back of the head of the patient.

For safety reasons, the remote stop button or kill switch 168 is provided to the patient and is preferably placed in the patient's hand. The patient is instructed that pressing of the button 168 will instantly stop the motion of the treatment table 121 during automatic adjustment of the backrest, cervical tilt or lumbar tilt as well as during treatment. Verification should also be made that the remote stop button cable 168*a* is plugged in and this aspect of the system should be tested daily.

Figure 44:
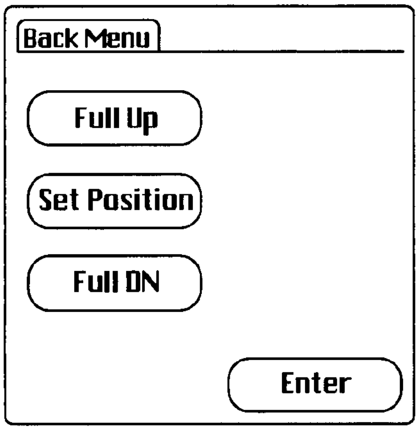

The palmtop computer or controller 134 is next used, as necessary, to adjust the backrest section 124 to the desired treatment position. This is done when the treatment table 121 has been initially positioned in the seated or upright position by selecting "Setup" so that the "Setup" screen of FIG. 43 is displayed, selecting "Backrest" so that the "Back" menu of FIG. 44 is displayed and then selecting "Full DN" and then "Enter." This provides automatic lowering of the treatment table 121 to the reclining position. Alternatively, the palmtop controller 134 is used to select the Back Menu of FIG. 44, select "Set Position" to call up the "Set Back Angle: screen of FIG. 45 and then to select and hold "Down" until the desired angle is displayed (e.g. 0° for fully reclined) is displayed and to select "Enter" to automatically lower backrest section 124 and cervical section 130 of the treatment table 121 to the specified position. Any setting from 0° to 90° can be entered and, as indicated above, a setting of 0° corresponds to a fully reclined position.

If necessary or desired, the calf support section 128 can be adjusted to a suitable position. In a specific implementation this is above, this is done by grasping calf support handles (not shown) to release the aforementioned releasable locking mechanism (not shown) and moving the calf support section 128 to the desired position. As discussed above, in a typical treatment position the patient lies on his or her back on the treatment table 121 with the lower legs elevated by the calf support section but in some instances it may not be desirable to so position the patient and this is, of course, up to the practitioner to decide. Moreover, in some treatments mentioned above, the patient lies on his or her side. For such treatments it may be desirable to position the calf support section 128 in the full reclining position, i.e., in the same plane as the treatment table 121.

Figure 46:
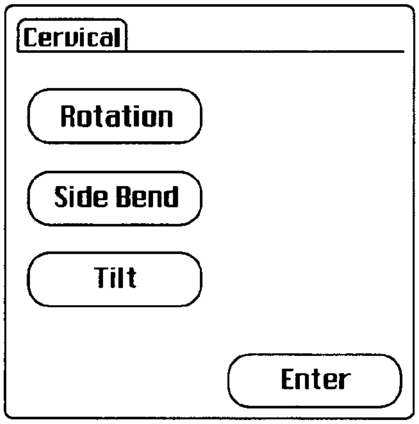

Turning to the cervical movements, if the cervical support section 130 is to be tilted, the palmtop computer 134 is used to actuate the tilting function. More specifically, this is done by first selecting "Setup" (FIG. 43) so that the "Setup" screen of FIG. 43 is displayed, by then selecting "Cervical" so that the Cervical menu of FIG. 46 is displayed and thereafter selecting "Tilt" and then using a further menu which is not illustrated, selecting and holding "Up" until the desired forward angle (from 0° to 45° in the specific implementation under consideration) is displayed. Next, "Enter" is selected on the non-illustrated menu and the cervical support section 130 is tilted forward to the desired angle of tilt, as discussed above.

Similarly, if the lumbar support section 126 is to be tilted, the palmtop controller or computer 134 is again used to activate the tilting function. More specifically, the controller 134 is used to first select "Setup" (FIG. 42) so that the "Setup" screen of FIG. 43 is displayed, is next used to select "Lumbar" so that the "Lumbar" menu (not shown) is displayed. The "Lumbar" menu is very similar to the "Cervical" menu and includes the same selections. By selecting "Tilt," a further Lumbar tilt menu (not shown) is displayed and the user selects and holds "Up" on that menu, until the desired forward angle is displayed. By then selecting "Enter" on that menu, the lumbar section 126 automatically tilts to the lumbar support forwardly to a selected angle of tilt (between 0° and 45°).

Figure 47:
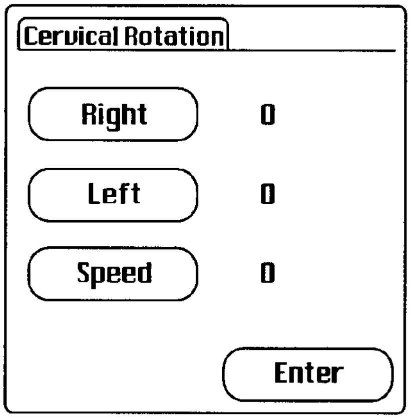

After the patient is positioned as desired on the treatment table 121, the practitioner can enter the treatment settings. To do this, using the palmtop controller 134, "Setup" is first selected from the menu of FIG. 42 so that the "Setup" screen of FIG. 43 is displayed. If cervical rotation or cervical side bending is desired, "Cervical" is selected and the "Cervical Screen" of FIG. 46 is displayed. For rotation, the "Rotation" is selected from the menu of FIG. 46 and the "Cervical Rotation" screen of FIG. 47 is displayed. The appropriate direction(s) magnitude and speed of cervical rotation are entered by making a corresponding selected ("Right," "Left," "Speed") and entering appropriate values using corresponding screens or menus called up by the particular selection. For side bending, "Side Bend" is selected and the inputs corresponding to those for "Rotation" are entered.

Similarly, if lumbar rotation and/or lumbar side bending is desired, "Lumbar" is selected and the "Lumbar" screen (not shown) is displayed. Again, the "Lumbar" screen is very similar to the "Cervical" screen of FIG. 46 and provides the same "Rotation," "Side Bend," "Tile" and "Enter" selections. If lumbar rotation is desired, "Rotation" is selected and the direction(s), magnitude and speed of lumbar rotation to be applied is entered. Similarly, if side bending is desired, "Side Bend" is selected and corresponding control parameters are entered.

Figure 48:
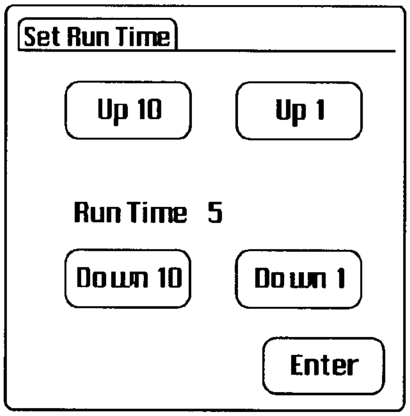

To select the time for the treatment procedure, "Time" is selected on the "Startup" screen of FIG. 43 and the "Set Run Time" screen of FIG. 48 is displayed. At this point, the time (in minutes) is entered for which the specified continuous passive motions are to be applied.

The various settings described above can be reviewed by selecting "Review" on the "Setup screen" of FIG. 43 so that the "Check and Start" screen of FIG. 42 is displayed. This permits review of the treatment settings to verify that the desired motions and their desired direction, magnitude and speed have been correctly entered.

To begin the treatment after all of the treatment settings have been entered and verified, the practitioner can begin the treatment. To start the treatment, the following steps are taken: (i) verify that the patient is holding the remote stop button or kill switch 168 and can operate the button 168 if necessary; (ii) verify that the patient's arms are either resting on arm rest cushions 158 of the arm rest 132 or are resting in a position that is distant from the moving surfaces; (iii) using the palmtop controller 134, the "Check and Start" screen of FIG. 42 is displayed; and (iv) "Start" on the screen of FIG. 42 is selected and the continuous passive motion treatment begins and will continue for the specified length of time.

The treatment is of course, monitored by the practitioner or other qualified person while the treatment is progressing. At the end of the treatment, the treatment table 121 can be returned to the seated position shown in FIGS. 26 and 27 (or another selected position) so that the patient can get up from the treatment table. To achieve this, the calf support section can be lowered to the stowed position shown in FIGS. 26 and 27. The procedure using the palmtop controller 134 would be similar to that described above as would that for lowering the cervical support 130 and the lumbar support 126. When the latter operations are completed, the backrest 124 and lowered cervical support 130 would be raised to the seated position (90°) or some selected angular position therebetween.

The user interface for the system is accessed from the "Home" screen (not shown) of the handheld palmtop controller 134. By clicking on a corresponding icon (not shown) on the "Home" screen, the "Check and Start" screen shown in FIG. 42 is displayed. This screen of FIG. 42 displays all of the treatment settings so that these settings can be readily reviewed before starting the treatment for a particular patient. The treatment settings of the "Check and Start" screen are as follows:

| Setting | Description |
|---|---|
| Backrest | Set the back rest angle from zero to 90 degrees. When the back rest angle is set at zero degrees, the subject is lying flat. When the back rest angle is set at 90 degrees, the subject is in an erect, seated position. |
| Time | The treatment time, in minutes. |
| Cervical | Rotation: The right and left rotation motions that will be applied to the cervical spine, and the speed at which the motions will be applied.<br>Side Bend: The right and left side bend motions that will be applied to the cervical spine, and the speed at which the motions will be applied.<br>Tilt: The angle at which the head will be inclined forward (relative to the body) during the treatment. |
| Lumbar | Rotation: The right and left rotation motions that will be applied to the lumbar spine, and the speed at which the motions will be applied.<br>Side Bend: The right and left side bend motions that will be applied to the lumbar spine, and the speed at which the motions will be applied.<br>Tilt: The angle at which the back will be tilted forward (relative to the thighs) during the treatment. |

As indicated above and shown in FIG. 42, the screen of FIG. 42 also includes the following two further operation buttons "SetUp" and "Start" which function as follows:

| Button | Description |
| --- | --- |
| SetUp | Allows the operator to enter a new value for the Backrest, Time, Cervical, and Lumbar treatment settings. |
| Start | Starts the CPM treatment by actuating cervical rotation and/or side bending (if specified) and lumbar rotation and/or side bending (if specified). |

As discussed above, the "Setup" screen is shown in FIG. 43 and allows the operator to modify the Backrest, Time, Cervical, and Lumbar treatment settings. The "Setup" screen contains five operation buttons as follows:

| Button | Description |
| --- | --- |
| Back Rest | Set the angle of the back rest. |
| Time | Set the treatment time. |
| Cervical | Display the screen for setting cervical rotation and side bend motions and for specifying the speed of each motion. |
| Lumbar | Display the screen for setting lumbar rotation and side bend motions and for specifying the speed of each motion. |
| Review | Display the "Check and Start" screen of FIG. 42 so that all of the treatment settings can be reviewed |

Figure 45:
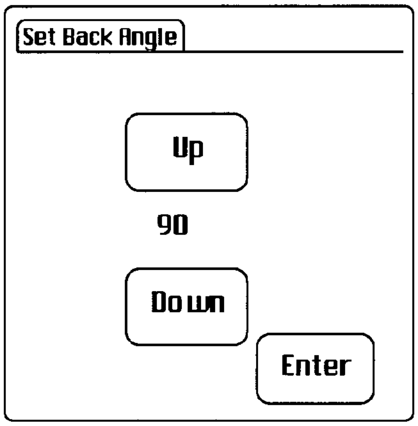

Turning now to the various treatment settings, and reviewing some of the operations discussed above, the backrest section 124 and cervical section 130, collectively referred to as the BackRest, can be raised or lowered together as described above between the fully reclined position (full down or 0°) shown in FIG. 25 and the select seated position (full up or 90°) shown in FIGS. 26 and 27 and to any position therebetween (e.g., 45°). As discussed hereinbefore, this is accomplished using the controller 134 by first selecting Back Rest from the "Set Screen" of FIG. 43 so as to display the "Back" menu shown in FIG. 44. If fully reclined or erect seated position is desired, the "Full DN" or "Full Up" buttons on the screen of FIG. 45 are selected whereas if an intermediate position is selected, the "Set Position" button on the screen of FIG. 44 is selected, a further "Set Back Angle" screen shown in FIG. 45 is displayed. The "Down" of the screen of FIG. 45 is selected and held to reduce the displayed setting. Similarly, Up" is selected on the screen of FIG. 45 and held to increase the displayed setting. When the desired setting is displayed, "Enter" is selected to immediately re-position the treatment table in the specified position.

As was also indicated above, the amount of cervical tilt can also be controlled. The term cervical tilt as used herein refers to the amount of forward bending of the neck provided during treatment and cervical tilt is controlled by controlling the angular position of tilt plate 228 of the cervical section 130. It is to be understood that cervical tilt is set at the beginning of the treatment and remains set throughout the treatment unless intentionally changed by the practitioner.

As indicated above, to set the cervical tilt, "Cervical" is selected from the "Setup" screen of FIG. 43 and the "Cervical" menu shown in FIG. 46 is displayed. By selecting "Tilt," a screen (not shown) similar to that of FIG. 45 is shown and the angle of tilt is controlled by selecting and holding an "Up" or "Down" button as described previously until a selected angle between 0° and 45° is indicated.

To set cervical rotation, i.e., rotation of cervical section 130 about a central pivot axis defined by shaft 226 as discussed above in connection with FIG. 34, "Rotation" is selected from the "Cervical" menu of FIG. 46 and the Cervical Rotation screen shown in FIG. 47 is displayed. As indicated above, rotation to the right or left can be selected for the patient, i.e., limited rotation to one side or the other as indicated by arrows A and B of FIG. 34, and this is done by selecting "Right" or "Left" on the screen of FIG. 47. The amount of rotation is selected using another screen (not shown) which is similar to that of FIG. 45 and which includes similar "Up" and "Down" (as opposed to "Left" and "Right") selection possibilities. An angle of between 0° and 30° can be selected in the particular implementation under consideration and the selection process is similar to that described above. Of course, in many instances, both "Right" and "Left" will be selected and the angle selected will be the same for both.

A similar screen (not shown) with similar "Up" and "Down" selections is used to select speed after "Speed" is selected on the screen of FIG. 47. The speed of rotation is in degrees per second and in the specific non-limiting implementation under consideration here, any setting from 0 to 15 can be selected.

As indicated above, cervical side bending can also be controlled. This involves side to side bending of the neck and the setting selected determines the amount and speed of left-side to right-side bending of the neck during treatment effected by pivoting of cervical section 130 about shaft 200 as described above relative to FIGS. 36 and 37.

Figure 49:
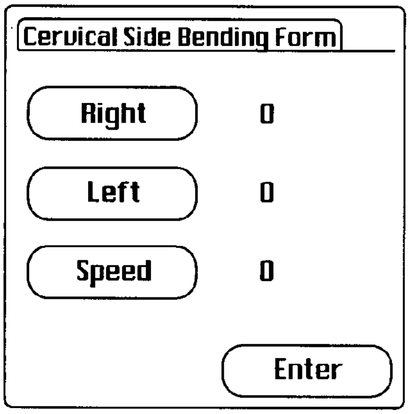

To set cervical side bending, "Side Bend" is selected from the "Cervical" menu of FIG. 43 to display a "Cervical Side Bend" screen which is shown in FIG. 49 and which is similar to that of FIG. 47. Depending on what side bending is to take place, "Right" or "Left" is selected, followed by "Enter." This causes a further screen (not shown) to be displayed similar to those described above (see FIG. 45), with "Up" and "Down" buttons, as described. This enables a side bending angle of 0° to 25° to be entered in the particular implementation under consideration.

The desired speed of the cervical side bending is set in a manner similar to that described above using a screen (not shown) containing "Up" and "Down" selections. In this implementation, the range for the speed of side bending is 0 to 15 degrees per second.

Turning now to the control of lumbar treatment procedures, using palmtop controller 134, this control is similar to that described above for cervical treatment and will be only briefly described. Lumbar tilt determines the forward inclination of the lower spine selected and, similar to cervical tilt, is set at the beginning of the treatment and is maintained throughout the treatment unless changed by the practitioner.

Lumbar tilt is set in basically the same way as cervical tilt using similar screens. The lumbar tilt plate 184 can be controlled to provide lumbar tilt at any angle between 0° and 45°, in this implementation.

Setting of lumbar rotation determines the magnitude and speed of the left-to-right rotation of the lower spine that is applied during treatment. The setting procedure is similar to that for cervical rotation and similar screens (not shown) are provided. In this implementation, rotation angle of 0° to 20° can be entered and a speed of 0 to 15 degrees per second can be entered.

Similar remarks apply to the setting of lumbar side bending. This setting determines the magnitude of the left-side-to-right-side bending of the lower spine that is applied during treatment. Lumbar side bending is set in basically the same way as cervical side bending and similar screens are used. A side bend angle of 0° to 20° and a speed of 0° to 15° can be entered.

Turning to setting of the treatment time, when the "Start" button of the screen of FIG. 42 is selected, one or more of the various motions described above, i.e., cervical rotation, cervical bending, lumbar rotation, and lumbar bending will, as specified by the practitioner, begin, and will proceed at the speed specified for that motion. The speed is set using the "Set Run Time" screen shown in FIG. 48 after "Time" is selected from the "Setup" screen of FIG. 43. The "Up 10" (course change), e.g., 10 minutes in this implementation or "Up 1" (fine change, e.g., 1 minute) is selected and held to increase the displayed run time while the "Down 10" and "Down 1" are selected and held to decrease the displayed run time. When the desired run time is displayed, "Enter" is selected. A run time of 5 to 195 minutes can be entered in this implementation.

As stated, all of the treatment settings can be reviewed by reviewing the "Check and Start" screen of FIG. 42.

In addition to the other safety features described above, various electronic or other sensors can be used to control motors of the motorized drives described to ensure that, in all circumstances, these motors will stop immediately in response to a patient or user alert (e.g., using kill switch 158) or upon a subsystem failure. For example, a sensor (not shown) is preferably provided which prevents the various therapeutic motions described above from being carried out when the calf support section 128 is in the stowed or down position, i.e., is in any lowered position, other than at least level with the treatment table 121. In another example, if there is a malfunction during raising or lowering of backrest section 132 (and associated cervical support section 130), the two sections will be stopped and will stay in the stopped position so as to prevent any uncontrolled movement thereof. In addition, the computer (not shown) also monitors each motor and motor subsection or drive arrangement to ensure that any abnormalities are detected and logged, and ultimately corrected. This logging of abnormalities or potential problems enables preventive maintenance to be carried out and also enables failure prediction so as to minimize any operational problems or errors.

Although the invention has been described above in relation to preferred exemplary embodiments thereof, it will be understood by those skilled in the art that variations and modifications can be effected in these preferred embodiments without departing from the scope and spirit of the invention. While many aspects of the exemplary embodiments are advantageous, it will be evident that, for example, different time settings, different ranges of motions and the like can be used and that, moreover, different drive mechanisms can be employed to effect the various of the desired movements and setup procedures described hereinabove.

Although the invention has been described above in relation to preferred embodiments thereof, it will be understood by those skilled in the art that variations and modifications can be effected in these preferred embodiments without departing from the scope and spirit of the invention.

What is claimed:

1. A continuous passive motion apparatus, said apparatus comprising:

a main support assembly for supporting at least part of the body of a user of the apparatus and including a first support member for, in one mode of use of the apparatus, providing a substantially horizontal support surface defining a plane and a second support member, for, in one mode of use of the apparatus, providing a substantially horizontal support surface disposed in said plane, said second support member being pivotable relative to said first support member such that pivoting movement of the second support member in said plane with respect to the first support member provides passive bending movement of a part of the body of a user supported by said second support member relative to a part of the body supported by said first support member, said second support member having a central, longitudinally extending axis and further being rotatable about said central axis to provide rotational movement of a part of the body supported by said second support member; and motorized drive means for, when activated, selectively providing said pivoting movement of said second support member relative to said first support member on a continuous, cyclically repeated basis to provide continuous passive bending movement of the part of the body supported by said second support member and selectively providing rotational movement of said second support member about said longitudinally extending axis on a continuous cyclically repeated basis to provide continuous passive rotational movement of the part of the body supported by said second support member.

2. A passive motion apparatus in accordance with claim 1 further comprising a calf support assembly connected to said main support assembly at one end of said main support assembly so as to support at least part of the legs of the user, said calf support assembly being connected to said main support assembly by an articulated connection for enabling said calf support assembly to be at least partially stowed away so as to enable a user to be positioned on said main support assembly without interference from said calf support assembly.

3. A passive motion apparatus in accordance with claim 2 wherein said calf support assembly includes a support platform and wherein said articulated connection is movable to a position wherein said platform is supported in a plane elevated with respect to the first-mentioned plane such that lower portions of the legs of the user are elevated with respect to the remainder of the body of the user and such that upper portions of the legs of the user extend at substantially right angles with respect to the lower portions of the legs and the trunk of the body of the user.

4. A passive motion apparatus in accordance with claim 3 wherein said articulated connection of said calf support assembly includes at least two pivotable links for enabling movement of said support platform into the first-mentioned plane and for enabling the spacing between said calf support assembly and said main support assembly to be varied.

5. A passive motion apparatus in accordance with claim 1 wherein said motorized drive means comprises at least one electric drive motor and control means for selectively controlling the operation of said at least one motor.

6. A passive motion apparatus in accordance with claim 5 wherein said control means comprises programmable means for controlling the at least one motor so as to control the amount of pivoting movement of said second support member relative to said first support member.

7. A passive motion apparatus in accordance with claim 6 wherein said control means includes a stop switch adapted to be operated by a user of the apparatus undergoing said passive movement to terminate the relative pivoting movement of said second support member.

8. A passive motion apparatus in accordance with claim 1 wherein said motorized drive means comprises a first motor for providing said pivoting movement and a second motor for providing said rotational movement.

9. A passive motion apparatus in accordance with claim 1 further comprising a pair of laterally spaced arm rests affixed to said main support assembly for movement relative thereto.

10. A passive motion apparatus in accordance with claim 1 wherein said main support assembly comprises a first part, and a second part selectively pivotable about a horizontal axis with respect to the first part between an inclined position and an upright position.

11. A passive motion apparatus in accordance with claim 10 wherein said second support section is adapted to support the lumbar region of the body of a user and forms at least a portion of said first part.

12. A passive motion apparatus in accordance with claim 11 further comprising a pair of laterally spaced arm rests affixed to said main support assembly for movement relative thereto such that said arms lie alongside the main support assembly in said inclined position and are disposed adjacent said second support section so as to form armrests in said upright position.

13. A passive motion apparatus in accordance with claim 1 wherein said second support member is selectively tiltable to a position wherein said second support member forms a non-zero angle with respect to said first support member.

14. A passive motion apparatus for providing passive motion of at least the lower trunk and legs of a user relative to the remainder of the body of the user, said apparatus comprising:

a first elevated support member for, in use, supporting at least an upper trunk portion of a user;

a second elevated support member, movable with respect to said first support member, and disposed, in one use of the apparatus, at a common level with, and adjacent to, said first support member, for, in use, supporting the lumbar region of the user;

a third elevated support member, selectively movable to a plane elevated with respect to said common level and disposed adjacent to said second support member, for supporting lower portions of the legs of the user; and motor means for, when activated, selectively providing continuous cyclically repeated pivotable movement of said second support member about a first pivot axis between spaced end positions so as to provide continuous passive bending motion of the lumbar region of the user and for, when activated, selectively providing continuous cyclically repeated, rotational movement of said second support member about a second, longitudinally extending pivot axis orthogonal to said first pivot axis so as to provide continuous passive rotational motion of the lumbar region of the user.

15. A passive motion apparatus in accordance with claim 14 further comprising a further elevated support member, movable with respect to said first support member and disposed, in one mode of use of the apparatus, at a common level with, and adjacent to, said first support member, for, in use, supporting at least a portion of the head of the user, said second support member being mounted for pivotable movement relative to said first support member, said motor means, when activated, selectively providing continuous cyclically repeated pivotable movement of said further support member about a vertical axis between spaced end positions so as to provide continuous passive bending motion of the cervical region of the body of the user.

16. A passive motion apparatus in accordance with claim 15 wherein said motor means comprises a separate motor and motor drive assembly for said second support member for, when activated, providing said continuous cyclically repeated rotational movement of the lumbar region of the user supported on said second support member.

17. A passive motion apparatus in accordance with claim 16 wherein said apparatus further comprises motorized cervical rotation means for said further support member for, when activated, providing continuous cyclically repeated rotational movement of the neck and head of a user between first and second end positions.

18. A passive motion apparatus in accordance with claim 15 wherein said further support member is selectively tiltable to a position wherein said further support member forms a non-zero angle with respect to said first support member.

19. A passive motion apparatus in accordance with claim 14 wherein said third elevated support member comprises a support platform and includes means for pivotably mounting said support platform with respect to said third support member so as to enable angular and longitudinal adjustment of the support platform relative to the first support member.

20. A passive motion apparatus in accordance with claim 14 wherein said second support member is selectively tiltable to a position wherein said second support member forms a non-zero angle with respect to said first support member.

21. A passive motion apparatus in accordance with claim 14 further comprising control means for said motor means for, when activated, simultaneously providing both said pivotable movement and said rotational movement.

22. A passive motion apparatus in accordance with claim 14 wherein said motor means, when activated, selectively provides continuous, cyclically repeated, pivotable movement of said second support member about a third pivot axis orthogonal to said first pivot axis and said second pivot axis so as to provide a continuous passive titling motion of the lumbar region of the user.

23. A continuous passive motion apparatus, said apparatus comprising:

a main support assembly for supporting at least part of the body of a user of the apparatus and including a first support member for providing a substantially horizontal support surface defining a first plane, a second support member for, in one configuration of the apparatus, providing a second support surface disposed in said plane, a third support member including for, in said one configuration of said apparatus, providing a third support surface disposed in said plane, said second and third support members each being pivotably mounted so as to be movable, in said one configuration, in said plane relative to said first support member such that pivoting movement of the second and third support members with respect to the first support member provides passive bending movement of a respective part of the body of a user supported by said second and third members relative to a part of the body supported by said first support member, said second and third support members each being further pivotably mounted about a respective central pivot axis thereof so as to enable rotation of the support surface thereof about said central pivot axis such that rotational movement of said second and third members provides passive rotational movement of a respective part of the body of a user supported by said first support member;

a leg support assembly connected to said main support assembly at one end of said main support assembly so as to support at least part of the legs of the user, said leg support assembly being movable to a second plane elevated with respect to said first plane;

motorized drive means for, when activated, selectively providing continuous cyclically repeated pivoting movement of said second and third support members about the respective vertical axes thereof relative to said first support member and selectively providing continuous cyclically repeated rotational movement of said second and third support members about the respective central pivot axes thereof relative to said first support member.

24. A passive motion apparatus in accordance with claim 23 wherein said motorized means comprises a first motor for providing pivoting movement of said second support member, a second motor for providing pivoting movement of said third support member, a third motor for providing rotational movement of said second support member, a fourth motor for providing rotational movement of said third support member and programmable means for controlling selective activation of said first, second, third and fourth motors.

25. A passive motion apparatus in accordance with claim 23 wherein said second support member is selectively tiltable to a position wherein said second elevated support member forms a non-zero angle with respect to said first support member.

26. A passive motion apparatus in accordance with claim 23 wherein said third support member is selectively tiltable to a position wherein said third support member forms a non-zero angle with respect to said first support member.

27. A continuous passive motion apparatus, said apparatus comprising:

a body support unit comprising:

at least one support member for, in use, supporting at least the upper trunk and head of a user;

a second support member, movable with respect to said at least one support member and disposed adjacent to said at least one support member, for, in use, supporting the lumbar region of the user;

a third support member, disposed adjacent to said second support member and movable to a different plane therefrom, for engaging the calf portions of the legs of the user; and motor means for, when activated, at least providing continuous cyclically repeated lateral pivoting movement of said second and third support members together, relative to said at least one support member;

a stationary base for supporting said body support unit; and means for selectively providing pivoting of said at least one support member of said body support unit relative to said stationary base and said second and third support members, between a first position wherein, in use, a user is supported in seated posture on the second support member of the said body support unit with the upper trunk and head resting against said at least one support member, and a second, substantially horizontal position wherein, in use, a user is supported in a reclining posture on said body support unit.

28. A passive motion apparatus in accordance with claim 27 wherein said at least one support member comprises a first support member for supporting the head of a user and a further support member for supporting the upper trunk of a user.

29. A passive motion apparatus in accordance with claim 27 wherein said at least one support member and said second support member are pivotable relative to each other so as to form a non-zero angle therebetween in the first position of said body support unit.

30. A passive motion apparatus in accordance with claim 27 wherein said second support member extends outwardly at a non-zero angle with respect to said at least one support member so as to act as a seat in said first position of said body support unit.

31. A passive motion apparatus in accordance with claim 27 wherein at least one support member of said body support unit includes a first support member for supporting the head of a user and a further support member for supporting at least the upper trunk of a user, and wherein said apparatus further comprises movement control means for providing continuous cyclically repeated lateral pivotable movement of the first support member with respect to said further support member.

32. A passive motion apparatus in accordance with claim 31 wherein said movement control means further comprises cervical rotation means for controlling movement of said first support member so as to provide rotational movement of the head and neck of the user.

33. A passive motion apparatus in accordance with claim 32 wherein said movement control means controls movement of said first member so as to produce continuous, cyclically repeated rotational movement of the head and neck of the user between first and second end positions.

34. A passive motion apparatus in accordance with claim 27 further comprising cervical rotation means for said first support member for, when activated, providing continuous, cyclically repeated rotational movement of the neck and head of a user between first and second end positions.

35. A passive motion apparatus in accordance with claim 27 further comprising control means for controlling movement of said second and third support members to produce continuous, cyclically repeated rotational movement between first and second end positions of the part of the body received on said second and third support members.

36. A passive motion apparatus in accordance with claim 35 wherein said control means comprises a handheld computer for enabling of control speed, direction and amount of pivoting movement and speed, direction and amount of rotational movement.

37. A passive motion apparatus in accordance with claim 36 wherein said handheld computer further enables setting of a time period for said pivoting movement and for said rotational movement.

38. A continuous passive motion apparatus, said apparatus comprising:

a main support assembly for supporting at least part of the body of a user of the apparatus and including first, second and third support members for supporting different parts of the body of the user, at least one of said support members being pivotably mounted and being movable relative to the remaining support members of the main support assembly such that movement of the at least one support member with respect to the remaining support members provides passive movement of a part of the body of a user supported by said at least one member relative to a part of the body supported by the remaining support members;

motorized drive means for, when activated, providing said movement of said at least one support member relative to said remaining support members on a continuous, cyclically repeated basis to provide continuous passive movement of the part of the body supported by said at least one support member;

said at least one of said support members of said main support assembly being adapted to support the head of a user thereon and said apparatus further comprising motorized cervical rotation means for said at least one support member of said main support assembly for, when activated, providing continuous, cyclically repeated, rotational movement of the at least one support member about a longitudinally extending rotational pivot axis so as to provide passive rotational movement of the neck and head of a user when the head of a user is supported on said at least one support member.

39. A passive motion apparatus in accordance with claim 38 further comprising a leg support assembly connected to said main support assembly at one end of said main support assembly and adjustable to support lower portions of the legs of the user in an elevated plane relative to said main support assembly such that the lower portions of the legs of the user are elevated with respect to the remainder of the body of the user.

40. A passive motion apparatus in accordance with claim 38 further comprising motorized cervical bending means for said at least one support member of said main support assembly for, when activated, providing continuous, cyclically repeated movement of the at least one support member about a further axis orthogonal to said rotational pivot axis so as to provide passive binding movement of the neck of a user when the head of a user is supported on said at least one support member.

41. A passive motion apparatus for providing passive motion of at least the tower trunk and legs of a user relative to the remainder of the body of the user, said apparatus comprising:

a first elevated support member for, in use, supporting at least an upper trunk portion of a user;

a second elevated support member, movable with respect to said first support member, and disposed, in one use of the apparatus, at a common level with, and adjacent to, said first support member, for, in use, supporting the lumbar region of the user;

a third elevated support member, selectively movable to a plane elevated with respect to said common level and disposed adjacent to said second support member, for supporting lower portions of the legs of the user; and motor means for, when activated, selectively providing continuous cyclically repeated pivotable movement of said second support member about a first pivot axis between spaced end positions so as to provide continuous passive bending motion of the lumbar region of the user and for, when activated, selectively providing continuous cyclically repeated, rotational movement of said second support member about a second, longitudinally extending pivot axis orthogonal to said first pivot axis so as to provide continuous passive rotational motion of the lumbar region of the user;

and comprising a further elevated support member, movable with respect to said first support member and disposed, in one mode of use of the apparatus, at a common level with, and adjacent to, said first support member, for, in use, supporting at least a portion of the head of the user, said second support member being mounted for pivotable movement relative to said first support member, said motor means, when activated, selectively providing continuous cyclically repeated pivotable movement of said further support member about a vertical axis between spaced end positions so as to provide continuous passive bending motion of the cervical region of the body of the user.

* * * * *